(12) United States Patent
Popovic et al.

(10) Patent No.: US 11,918,404 B2
(45) Date of Patent: Mar. 5, 2024

(54) CONTROL OF ANATOMICAL IMAGE ACQUISITION USING PHYSIOLOGICAL INFORMATION

(71) Applicant: KONINKLIJKE PHILIPS N.V., Eindhoven (NL)

(72) Inventors: Aleksandra Popovic, Boston, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/134,505

(22) Filed: Apr. 13, 2023

(65) Prior Publication Data

US 2023/0248330 A1    Aug. 10, 2023

Related U.S. Application Data

(63) Continuation of application No. 16/470,265, filed as application No. PCT/EP2017/083324 on Dec. 18, 2017, now Pat. No. 11,653,889.

(Continued)

(51) Int. Cl.
*A61B 8/12* (2006.01)
*A61B 1/00* (2006.01)
(Continued)

(52) U.S. Cl.
CPC .......... *A61B 6/542* (2013.01); *A61B 1/00006* (2013.01); *A61B 1/000094* (2022.02);
(Continued)

(58) Field of Classification Search
CPC ............ A61B 1/00009; A61B 1/00006; A61B 5/6843; A61B 8/12; A61B 8/42; A61B 8/543
See application file for complete search history.

(56) References Cited

U.S. PATENT DOCUMENTS 5,906,578 A    5/1999  Rajan
6,425,865 B1   7/2002  Salcudean
(Continued)

FOREIGN PATENT DOCUMENTS

JP    2009142518 A    7/2009
JP    2014073271 A    4/2014
(Continued)

OTHER PUBLICATIONS

Wang et al., "Robotic Ultrasound: View Planning, Tracking, and Automatic Acquisition of Transesophageal Echocardiography", IEEE Robotics & Automation Magazine., vol. 23, No. 4, Nov. 7, 2016.
(Continued)

*Primary Examiner* — Colin T. Sakamoto

(57) ABSTRACT

An imaging device positioning system for monitoring an anatomical region (10). The imaging device positioning system employs an imaging device (20) for generating an image (21) of an anatomical region (10). The imaging device positioning system further employs an imaging device controller (30) for controlling a positioning of the imaging device (20) relative to the anatomical region (10). During a generation by the imaging device (20) of the image (21) of the anatomical region (10), the imaging device controller (30) adapts the positioning of the imaging device (20) relative to the anatomical region (10) to a physiological condition of the anatomical region (10) extracted from the image (21) of the anatomical region (10).

20 Claims, 14 Drawing Sheets

Related U.S. Application Data

(60) Provisional application No. 62/436,205, filed on Dec. 19, 2016.

(51) Int. Cl.
*A61B 5/00* (2006.01)
*A61B 6/00* (2006.01)
*A61B 8/00* (2006.01)

(52) U.S. Cl.
CPC .............. *A61B 5/6843* (2013.01); *A61B 8/12* (2013.01); *A61B 8/42* (2013.01); *A61B 8/543* (2013.01)

(56) References Cited

U.S. PATENT DOCUMENTS

| | | |
|---|---|---|
| 2010/0276471 A1 | 2/2010 | Chujoh et al. |
| 2011/0264983 A1 | 10/2011 | Yoshida et al. |
| 2011/0313280 A1 | 12/2011 | Govari et al. |
| 2012/0143028 A1 | 6/2012 | Park et al. |
| 2013/0123577 A1 | 5/2013 | Ho et al. |
| 2014/0046166 A1 | 2/2014 | Tokita |
| 2015/0182287 A1 | 7/2015 | Guthart et al. |
| 2016/0015259 A1 | 1/2016 | Mody et al. |
| 2017/0202537 A1 | 7/2017 | Ippolito et al. |

FOREIGN PATENT DOCUMENTS

| | | |
|---|---|---|
| WO | 2013/080124 | 6/2013 |
| WO | 2015/110937 | 7/2015 |
| WO | 2015/110943 | 7/2015 |

OTHER PUBLICATIONS

Mathur et al., "Transoesophageal Echocardiography Related Complications" Indian Journal of Anasthesia 2009; 53(5): pp. 567-574 (Year: 2009).

Abolmaesumi et al., "Image-Guided Control of a Robot for Medical Ultrasound" IEEE Transactions on Robotics and Automatoin, vol. 18, No. 1, Feb. 2002 (Year: 2002).

International Search Report and Written Opinion dated Mar. 23, 2018 for International Application No. PCT/EP2017/083324 filed Dec. 18, 2017.

CONTROL OF ANATOMICAL IMAGE ACQUISITION USING PHYSIOLOGICAL INFORMATION

CROSS-REFERENCE TO RELATED APPLICATIONS

This application is a continuation application of U.S. application Ser. No. 16/470,265, filed on Jun. 17, 2019, which is a U.S. National Phase application under U.S.C. § 371 of International Application No. PCT/EP2017/083324 filed Dec. 18, 2017, which claims the benefit of U.S. Provisional Patent Application Ser. No. 62/436,205, filed Dec. 19, 2016.

FIELD OF THE INVENTION

The inventions of the present disclosure generally relate to image device monitoring systems (e.g., Zura-EVO™ 1, CardioQ-EM+ and USCOM®, etc.). The inventions of the present disclosure more particularly relate to improving such image device monitoring systems by providing control of anatomical image acquisition using physiological information (e.g., ejection fraction, cardiac output, IVC/SVC diameter for fluid status, Doppler flow to an organ, etc.).

BACKGROUND OF THE INVENTION

Currently, hemodynamic monitoring as known in the art may involve a continuous ultrasound image acquisition over a specified period of time (e.g., 72 hours) or a fixed periodic ultrasound image acquisition. While advantageous for patient evaluation purposes, there are several drawbacks to such hemodynamic monitoring.

First, continuous ultrasound acquisition does not comply with an As Low As Reasonably Acceptable (ALARA) clinical practice, which such noncompliance exposes a patient to potential harm during the continuous ultrasound acquisition.

Second, continuous contact by an ultrasound transducer during a continuous ultrasound acquisition may cause tissue irritation for a patient, especially continuous contact by a Trans-esophageal (TEE) ultrasound probe on an esophagus of the patient for an ultrasound image monitoring of a cardiac function of the patient.

Third, a fixed periodic ultrasound acquisition with a pre-defined frequency does not adapt to current physiological conditions of the patient and any dynamic changes to such physiological conditions of the patient.

SUMMARY OF THE INVENTION

To improve upon ultrasound monitoring systems, the present disclosure provides inventions for controlling an anatomical image acquisition based on physiological parameters of a patient extracted from an imaging of the patient to thereby minimize a degree of exposure by the patient to the imaging.

One embodiment of the inventions of the present disclosure is an imaging device positioning system for monitoring an anatomical region.

The imaging device positioning system employs an imaging device for generating an image of an anatomical region.

The imaging device positioning system further employs a imaging device controller for controlling a positioning of the imaging device relative to the anatomical region. During a generation by the imaging device of the image of the anatomical region, the imaging device controller adapts the positioning of the imaging device relative to the anatomical region to one or more physiological conditions of the anatomical region extracted from the image of the anatomical region.

More particularly, the imaging device controller may cyclically adapt the positioning of the imaging device relative to the anatomical region between an imaging position and a non-imaging position based on the physiological condition(s) of the anatomical region extracted from the image of the anatomical region.

A second embodiment of the inventions of the present disclosure is the imaging device controller employing a physiological condition extractor and a imaging device positioner.

In operation, a physiological condition extractor generates physiological parameter data informative of the physiological condition(s) of the anatomical region extracted from the image of the anatomical region generated by the imaging device, and the imaging device positioner controls a positioning of the imaging device relative to the anatomical region.

In response to the physiological parameter data, the imaging device positioner further adapts the positioning of the imaging device relative to the anatomical region to the physiological condition(s) of the anatomical region extracted from the image of the anatomical region.

A third embodiment of the inventions of the present disclosure an imaging device positioning method of operating the imaging device positioning system for monitoring an anatomical region.

The imaging device positioning method involves the imaging device generating an image of an anatomical region, and the imaging device controller controlling a positioning of the imaging device relative to the anatomical region.

The imaging device positioning method further involves the imaging device controller adapts the positioning of the imaging device relative to the anatomical region to the physiological condition(s) of the anatomical region extracted from the image of the anatomical region generated by the imaging device.

For purposes of describing and claiming the inventions of the present disclosure:

(1) the term "imaging device" broadly encompasses all imaging devices, as known in the art of the present disclosure and hereinafter conceived, for imaging an anatomical region including, but not limited to:
 (a) an ultrasound transducer of any type including, but not limited to, a Transesophageal echocardiography (TEE) probe, an Intra-cardiac probe (ICE), an intra-nasal probe, an endobronchial probe, a laparoscopic probe, and an intravascular ultrasound (IVUS) probe;
 (b) an X-ray gantry of any type including, but not limited to, a C-shape X-ray gantry; and
 (c) a flexible or rigid scope of any type, including, but not limited to, an endoscope, an arthroscope, a bronchoscope, a choledochoscope, a colonoscope, a cystoscope, a duodenoscope, a gastroscope, a hysteroscope, a laparoscope, a laryngoscope, a neuroscope, an otoscope, a push enteroscope, a rhinolaryngoscope, a sigmoidoscope, a sinuscope, thorascope, and a nested cannula with imaging capability;

(2) an adaptation of a positioning of an imaging device relative to the anatomical region to physiological condition(s) of the anatomical region extracted from an image of the anatomical region involves:

(a) an increase in an imaging of the anatomical region by the imaging device in view of any deterioration of the physiological condition(s) of the anatomical region as delineated in the physiological parameter data; and (b) a decrease in an imaging of the anatomical region by the imaging device in view of any improvement of the physiological condition(s) of the anatomical region as delineated in the physiological parameter data;

(3) the term "physiological condition" broadly encompasses any physiological condition of an anatomical region extractable from an ultrasound image of an anatomical region. A non-limiting example is a physiological condition of a thoracic region including an ejection fraction, a cardiac output, a IVC/SVC diameter for fluid status, and a Doppler flow to an organ;

(4) the term "imaging positioning" broadly encompasses a designated positioning of an imaging device internal or external to an anatomical region whereby an imaging functionality of the imaging device is activated to image the anatomical region as known in the art of the present disclosure;

(5) the term "non-imaging positioning" broadly encompasses a designated positioning of an imaging device internal or external to an anatomical region whereby an imaging functionality of the imaging device is deactivated to image the anatomical region as known in the art of the present disclosure;

(6) the term "an image device positioning system" broadly encompasses all image device monitoring systems, as known in the art of the present disclosure and hereinafter conceived, incorporating the inventive principles of the present disclosure for visually monitoring an anatomical region. Examples of known image device monitoring systems include, but are not limited to, Zura-EVO™ 1, CardioQ-EM+ and USCOM®;

(7) the term "image device positioning method" broadly encompasses all image device monitoring methods, as known in the art of the present disclosure and hereinafter conceived, incorporating the inventive principles of the present disclosure for visually monitoring an anatomical region. Examples of known ultrasound monitoring methods include, but are not limited to, the Hemodynamic management (hTEE), Oesophageal Doppler monitoring, and non-invasive ultrasound Doppler monitoring;

(8) the term "imaging device controller" broadly encompasses all structural configurations of an application specific main board or an application specific integrated circuit housed employed within or linked to an image device positioning system of the present disclosure for controlling an application of various inventive principles of the present disclosure related to an ultrasound imaging of an anatomical region as subsequently exemplarily described herein. The structural configuration of the controller may include, but is not limited to, processor(s), computer-usable/computer readable storage medium(s), an operating system, application module(s), peripheral device controller(s), interface(s), bus(es), slot(s) and port(s);

(9) the term "application module" broadly encompasses a component of an ultrasound probe controller or a robot controller consisting of an electronic circuit and/or an executable program (e.g., executable software and/or firmware stored on non-transitory computer readable medium(s)) for executing a specific application; and

(10) the terms "signal", "data", and "command" broadly encompasses all forms of a detectable physical quantity or impulse (e.g., voltage, current, or magnetic field strength) as understood in the art of the present disclosure and as exemplary described herein for communicating information and/or instructions in support of applying various inventive principles of the present disclosure as subsequently described herein. Signal/data/command communication between components of the present disclosure may involve any communication method, as known in the art of the present disclosure and hereinafter conceived, including, but not limited to, signal/data/command transmission/reception over any type of wired or wireless medium/datalink and a reading of signal/data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1:
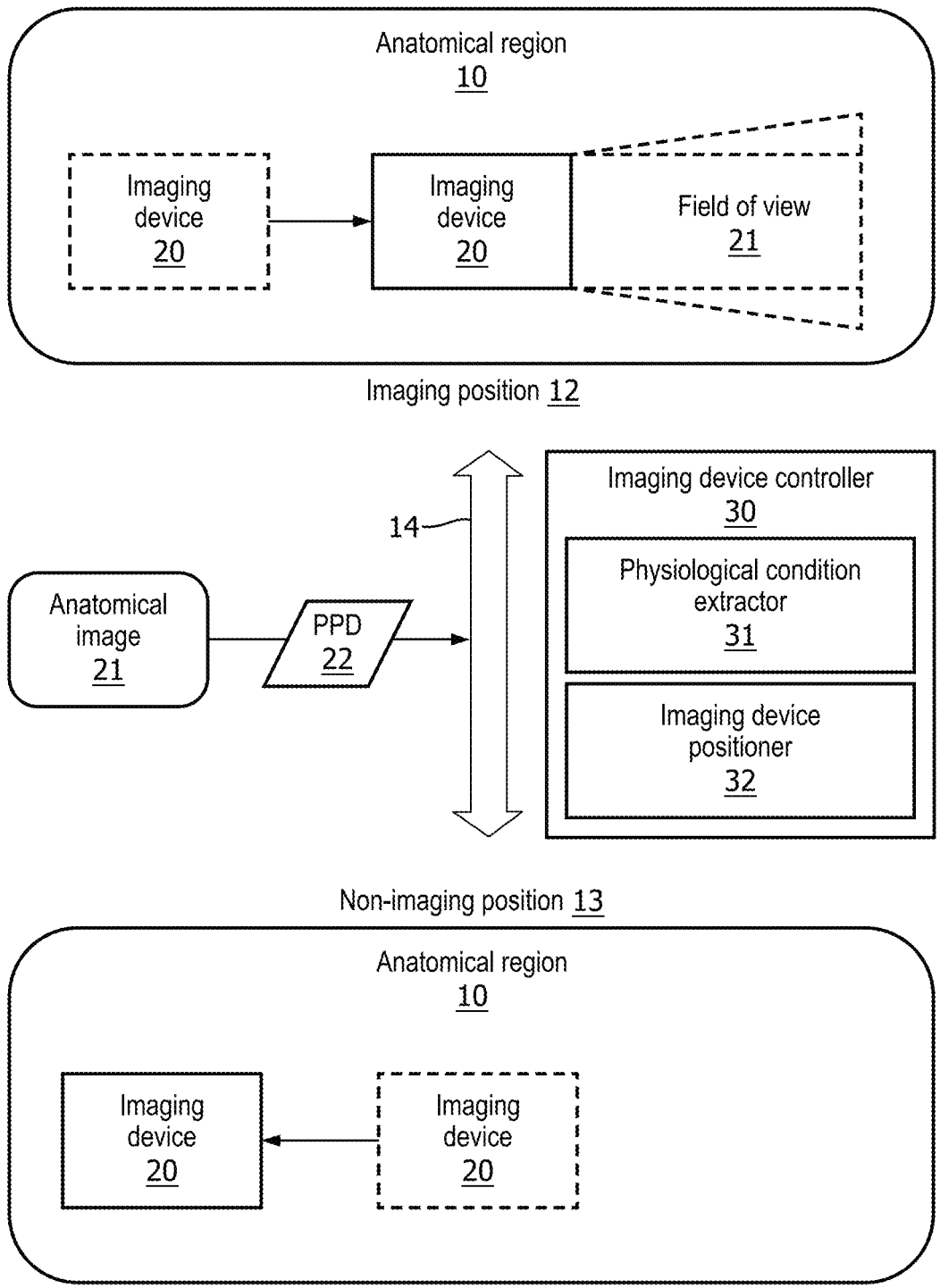
FIG. 1 illustrates an exemplary positioning of an imaging device within an anatomical region in accordance with the inventive principles of the present disclosure.

To facilitate an understanding of the inventions of the present disclosure, the following description of FIG. 1 teaches basic inventive principles of a positioning of an imaging device within an anatomical region in accordance with the inventive principles of the present disclosure. From this description of FIG. 1, those having ordinary skill in the art will appreciate how to apply the inventive principles of the present disclosure to practice numerous and various embodiments of positioning of an imaging device internal to or external to an anatomical region in accordance with the inventive principles of the present disclosure.

In practice, the inventions of the present disclosure are applicable to any anatomical region including, but not limited to, a cephalic region, a cervical region, a thoracic region, an abdominal region, a pelvic region, a lower extremity and an upper extremity. Also in practice, the inventions of the present disclosure are applicable to any type of anatomical structure including, but not limited to, tissue and bone, healthy or unhealthy.

Referring to FIG. 1, an imaging position 12 of the present disclosure encompasses a designated position of an imaging device 20 within an anatomical region 10 (e.g., an ultrasound transducer or a scope) whereby an imaging capability of imaging device 20 is activated for imaging a spatial area and/or of features and structures of anatomical region 10 within a field of view 21 of imaging device 20. Alternatively, imaging positon 12 may encompass a designated position of imaging device 20 external to anatomical region 10 (e.g., an X-ray gantry) whereby an imaging capability of imaging device 20 is activated for imaging a spatial area and/or of features and structures of anatomical region 10 within a field of view 21 of imaging device 20.

Conversely, a non-imaging position 13 of the present disclosure encompasses a designated position of an imaging device 20 within an anatomical region 10 (e.g., an ultrasound transducer or a scope) whereby an imaging capability of imaging device 20 is deactivated for minimizing any contact of imaging device 20 to a structure of anatomical region 10 and/or for reducing exposure of anatomical region 10 to any radiation/energy emitted by imaging device 20 for purposes of imaging anatomical region 10. Alternatively, imaging positon 13 may encompass a designated position of imaging device 20 external to anatomical region 10 (e.g., an X-ray gantry) whereby an imaging capability of imaging device 20 is deactivated for minimizing any contact of imaging device 20 to a structure of anatomical region 10 and/or for reducing exposure of anatomical region 10 to any radiation/energy emitted by imaging device 20 for purposes of imaging anatomical region 10.

Still referring to FIG. 1, a periodic or irregular cycling 14 of imaging device 20 between imaging position 12 and non-imaging position 13 involves a cyclical arrangement of imaging position 12 and non-imaging position 13 at a fixed or variable frequency and/or a fixed or variable duty cycle for purposes of visually monitoring a specific aspect of anatomical region 10 while minimizes any contact imaging device 20 to a structure of anatomical region 10 and/or for reducing exposure of anatomical region 10 to any radiation/energy emitted by imaging device 20 for purposes of imaging anatomical region 10.

To this end, an imaging device controller 30 employs a physiological condition extractor 31 for extracting physiological parameter data 22 from an anatomical image 21 of the anatomical region 10 generated by imaging device 20 whereby physiological parameter data 22 is informative of one or more physiological conditions of anatomical region 10 as will be further explained herein. For example, if anatomical region 10 is a thoracic region, then the physiological condition(s) of the thoracic region may be an ejection fraction, a stroke volume, a cardiac output, an IVC/SVC diameter for fluid status and/or a Doppler flow to an organ.

In practice, as would be appreciated by those having ordinary skill in the art of the present disclosure, any extraction technique known in the art may be implemented in dependence upon the type of physiological condition(s) being extracted from anatomical image 21 of the anatomical region 10.

Imaging device controller 30 further employs an imaging device positioner 32 for controlling an adaption of cycling 14 of a positioning of imaging device 20 to the physiological condition(s) of anatomical region 10 extracted from anatomical image 21 of the anatomical region 10. In practice, the adaption of cycling 14 of a positioning of imaging device 20 may include an increase to the fixed/variable frequency and/or the fixed/variable duty cycle of imaging position 12 in view of any deterioration of the physiological condition(s) of the anatomical region as delineated in the physiological parameter data 22, or conversely a decrease to the fixed/variable frequency and/or the fixed/variable duty cycle of imaging position 12 in view of any improvement of the physiological condition(s) of the anatomical region as delineated in the physiological parameter data 22.

Concurrently or alternatively in practice, the adaption of cycling 14 may include an increase to a degree of contact force between imaging device 20 and an anatomical structure of anatomical region 10 in view of any deterioration of the physiological condition(s) of the anatomical region as delineated in the physiological parameter data 22 to thereby facilitate a higher quality of imaging of anatomical region 10, or conversely a decrease to a degree of contact force between imaging device 20 and an anatomical structure of anatomical region 10 in view of any improvement of the physiological condition(s) of the anatomical region as delineated in the physiological parameter data 22 to thereby facilitates an acceptable quality of imaging of anatomical region 10 at a lesser degree of contact.

Generally, any deterioration or any improvement of the physiological condition(s) of the anatomical region may be delineated in the physiological parameter data 22 by any technique providing a definitive indication of such deterioration or improvement. More particularly in practice, any deterioration or any improvement of the physiological condition(s) of the anatomical region may be delineated by one or more thresholds established relative to the physiological parameter data 22 as will be further described herein. Concurrently or alternatively in practice, any deterioration or any improvement of the physiological condition(s) of the anatomical region may be delineated by a negative slope or a positive slope of the physiological parameter data 22 over a specified time period as will be further described herein.

Figure 2:
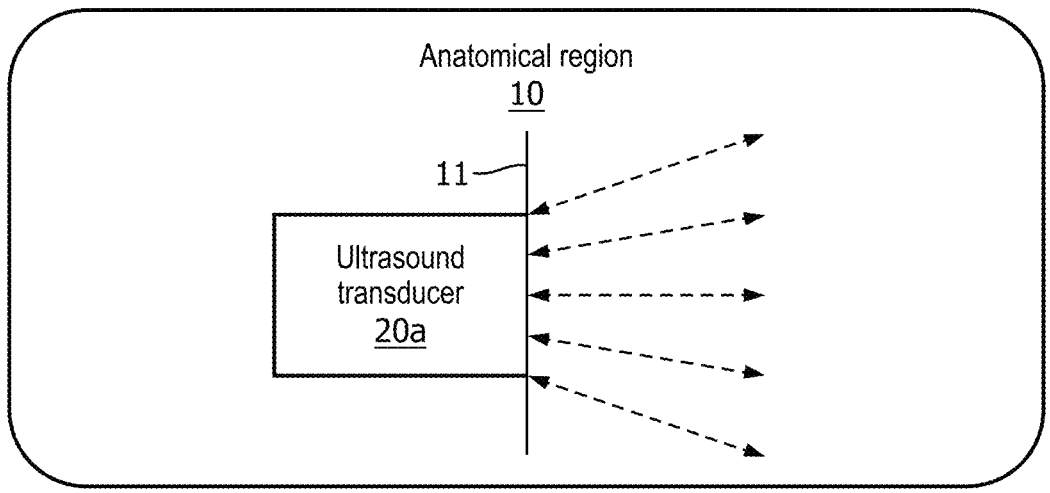
FIG. 2 illustrates an exemplary positioning of an ultrasound transducer within an anatomical region in accordance with the inventive principles of the present disclosure.
Figure 2:
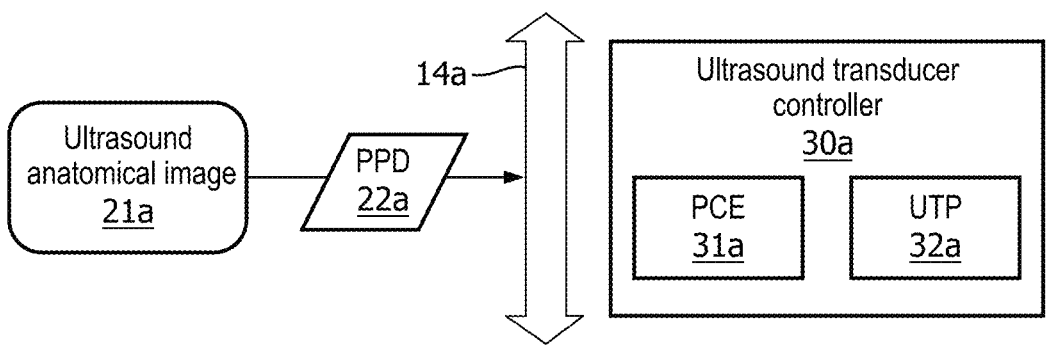
Figure 2:
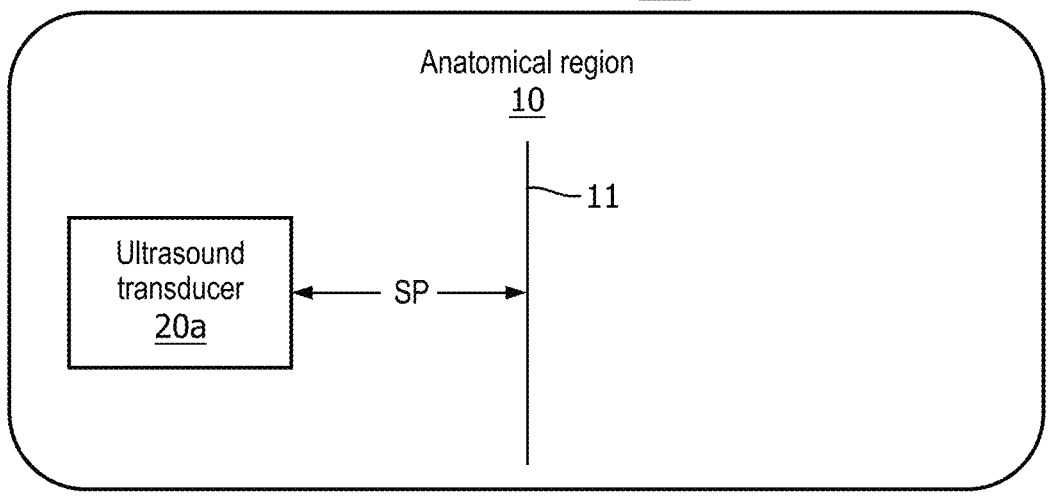

To facilitate a further understanding of the inventions of the present disclosure, the following description of FIG. 2 teaches basic inventive principles of a positioning of an ultrasound transducer within an anatomical region in accordance with the inventive principles of the present disclosure. From this description of FIG. 2, those having ordinary skill in the art will appreciate how to apply the inventive principles of the present disclosure to practice numerous and various embodiments of positioning of an ultrasound transducer internal to or external to an anatomical region in accordance with the inventive principles of the present disclosure.

Referring to FIG. 2, an imaging position 12a of the present disclosure encompasses a positioning within an anatomical region 10 of an ultrasound transducer 20a in direct or indirect contact with an anatomical structure 11 whereby ultrasound transducer 20a applies a force/counterforce to the anatomical structure 11 to a degree sufficient to facilitate an ultrasound imaging of the anatomical region 10 as exemplarily symbolized by the bi-directional dashed arrows.

Conversely, a non-imaging position 13a of the present disclosure encompasses a positioning within anatomical region 10 of ultrasound transducer 20a in direct or indirect contact with anatomical structure 11 whereby ultrasound transducer 20a is not applying a force/counterforce to the anatomical structure 11 to a degree sufficient to facilitate an ultrasound imaging of the anatomical region 10 (not shown in FIG. 2) or encompasses a spatial positioning SP between ultrasound transducer 20a and anatomical structure 11 as shown in FIG. 2, and preferably to minimize the force/counterforce imparted on the anatomical structure 11/or reducing the imparted force below a defined threshold.

Still referring to FIG. 2, a periodic or irregular cycling 14a of ultrasound transducer 20a between imaging position 12a and non-imaging position 13a involves a cyclical arrangement of imaging position 12a and non-imaging position 13a at a fixed or variable frequency and/or a fixed or variable duty cycle for purposes of visually monitoring a specific aspect of anatomical region 10 while minimizes any contact ultrasound transducer 20a to a structure of anatomical region 10 and/or for reducing exposure of anatomical region 10 to any radiation/energy emitted by ultrasound transducer 20a for purposes of imaging anatomical region 10.

To this end, an ultrasound transducer controller 30a employs a physiological condition extractor 31a for extracting physiological parameter data 22a from an anatomical image 21a of the anatomical region 10 generated by ultrasound transducer 20a whereby physiological parameter data 22a is informative of one or more physiological conditions of anatomical region 10 as will be further explained herein. For example, if anatomical region 10 is a thoracic region, then the physiological condition(s) of the thoracic region may be an ejection fraction, a stroke volume, a cardiac output, an IVC/SVC diameter for fluid status and/or a Doppler flow to an organ.

In practice, as would be appreciated by those having ordinary skill in the art of the present disclosure, any extraction technique known in the art may be implemented in dependence upon the type of physiological condition(s) being extracted from anatomical image 21a of the anatomical region 10.

Ultrasound transducer controller 30a further employs an ultrasound transducer positioner 32a for controlling an adaption of cycling 14a of a positioning of ultrasound transducer 20a to the physiological condition(s) of anatomical region 10 extracted from anatomical image 21a of the anatomical region 10. In practice, the adaption of cycling 14a of a positioning of imaging device 20 may include an increase to the fixed/variable frequency and/or the fixed/variable duty cycle of imaging position 12a in view of any deterioration of the physiological condition(s) of the anatomical region as delineated in the physiological parameter data 22a, or conversely a decrease to the fixed/variable frequency and/or the fixed/variable duty cycle of imaging position 12a in view of any improvement of the physiological condition(s) of the anatomical region as delineated in the physiological parameter data 22a.

Concurrently or alternatively in practice, the adaption of cycling 14a may include an increase to a degree of contact force between ultrasound transducer 20a and an anatomical structure of anatomical region 10 in view of any deterioration of the physiological condition(s) of the anatomical region as delineated in the physiological parameter data 22a to thereby facilitate a higher quality of imaging of anatomical region 10, or conversely a decrease to a degree of contact force between ultrasound transducer 20a and an anatomical structure of anatomical region 10 in view of any improvement of the physiological condition(s) of the anatomical region as delineated in the physiological parameter data 22a to thereby facilitates an acceptable quality of imaging of anatomical region 10 at a lesser degree of contact.

Generally, any deterioration or any improvement of the physiological condition(s) of the anatomical region may be delineated in the physiological parameter data 22a by any technique providing a definitive indication of such deterioration or improvement as known in the art of the present disclosure. More particularly in practice, any deterioration or any improvement of the physiological condition(s) of the anatomical region may be delineated by one or more thresholds established relative to the physiological parameter data 22a as will be further described herein. Concurrently or alternatively in practice, any deterioration or any improvement of the physiological condition(s) of the anatomical region may be delineated by a negative slope or a positive slope of the physiological parameter data 22a over a specified time period as will be further described herein.

Figure 3:
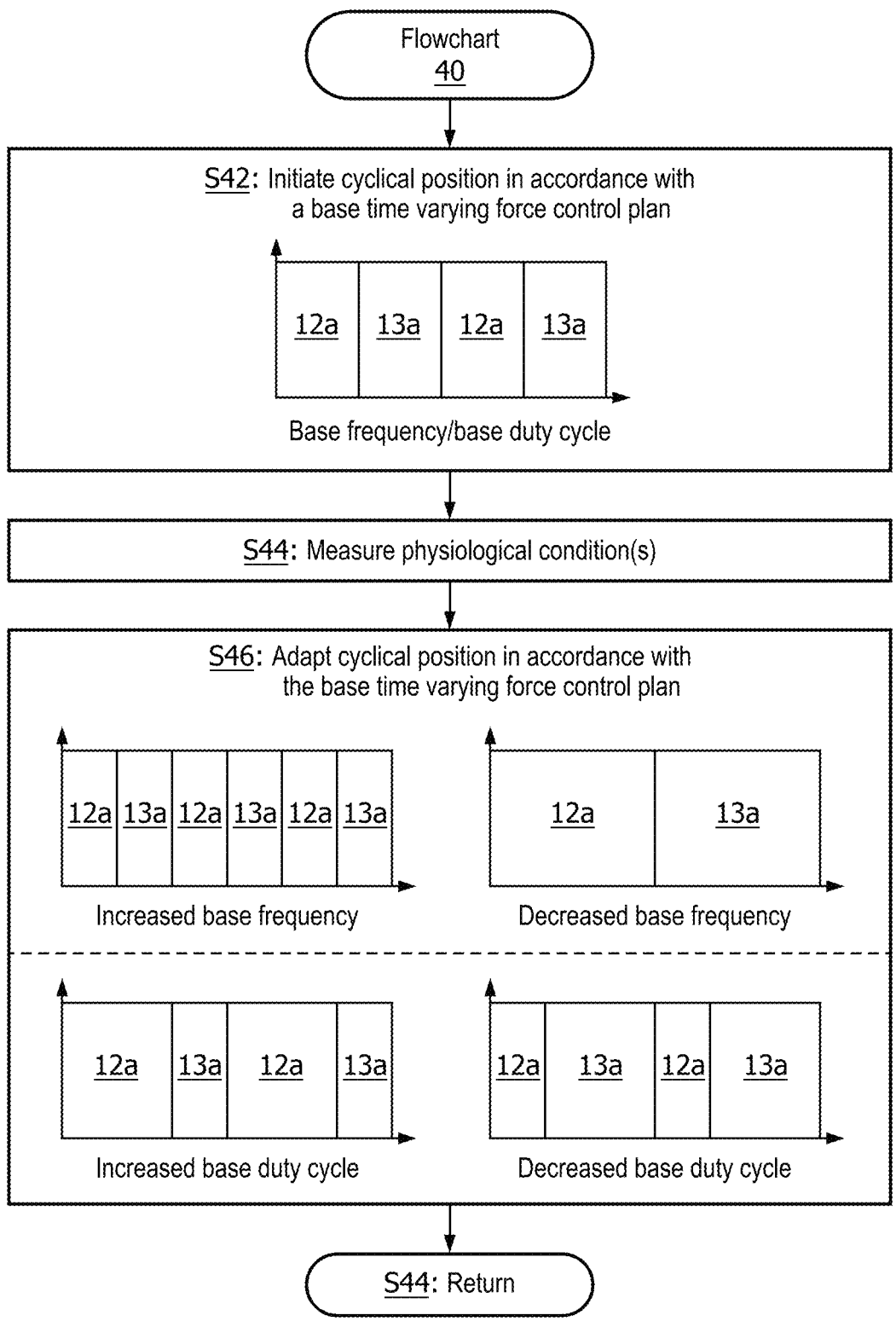
FIG. 3 illustrates an exemplary embodiment of a flowchart representative of an ultrasound positioning method in accordance with the inventive principles of the present disclosure.
Figure 4A:
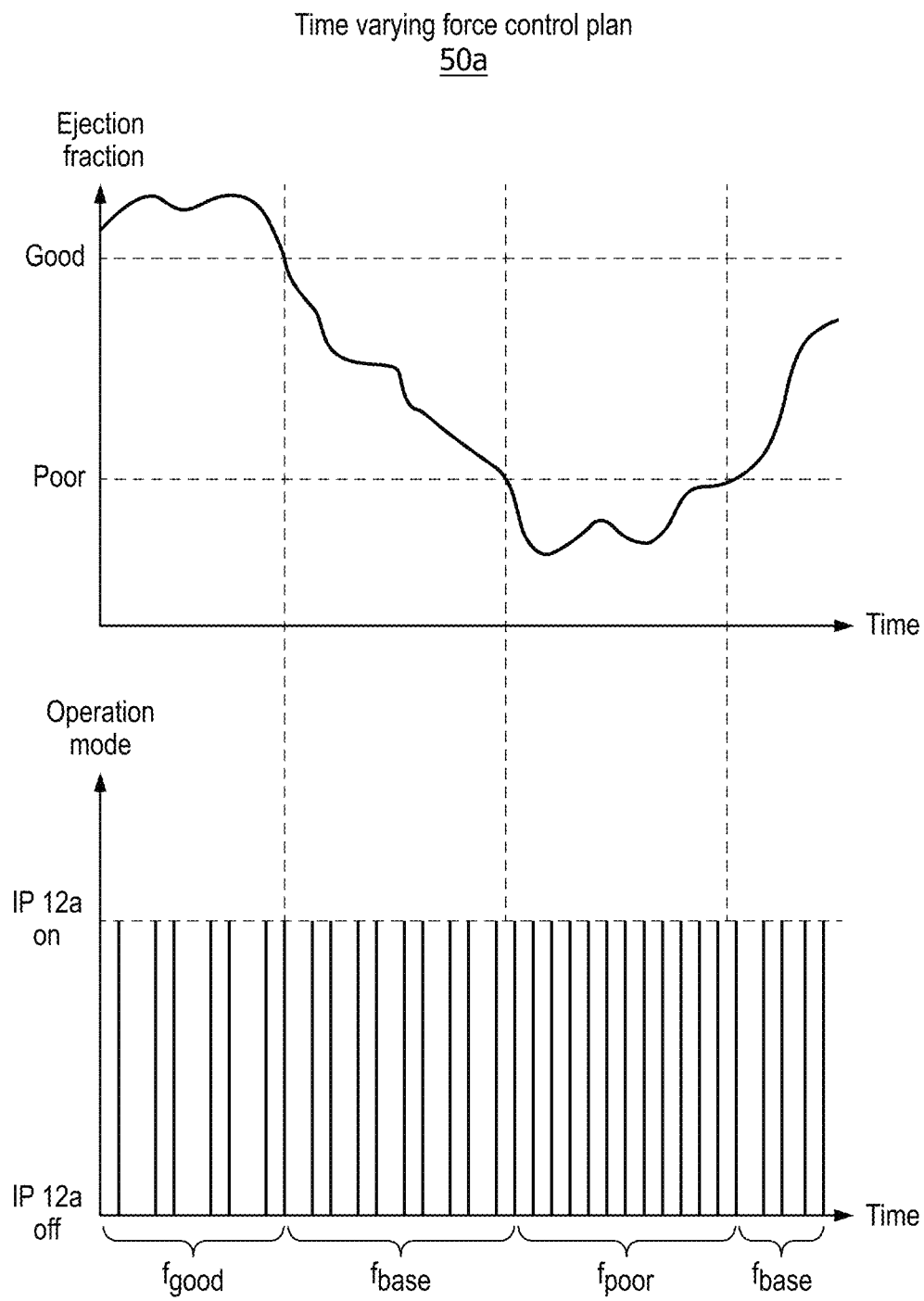
FIGS. 4A and 4B illustrates exemplary time varying force control plans in accordance with the inventive principles of the present disclosure.
Figure 4B:
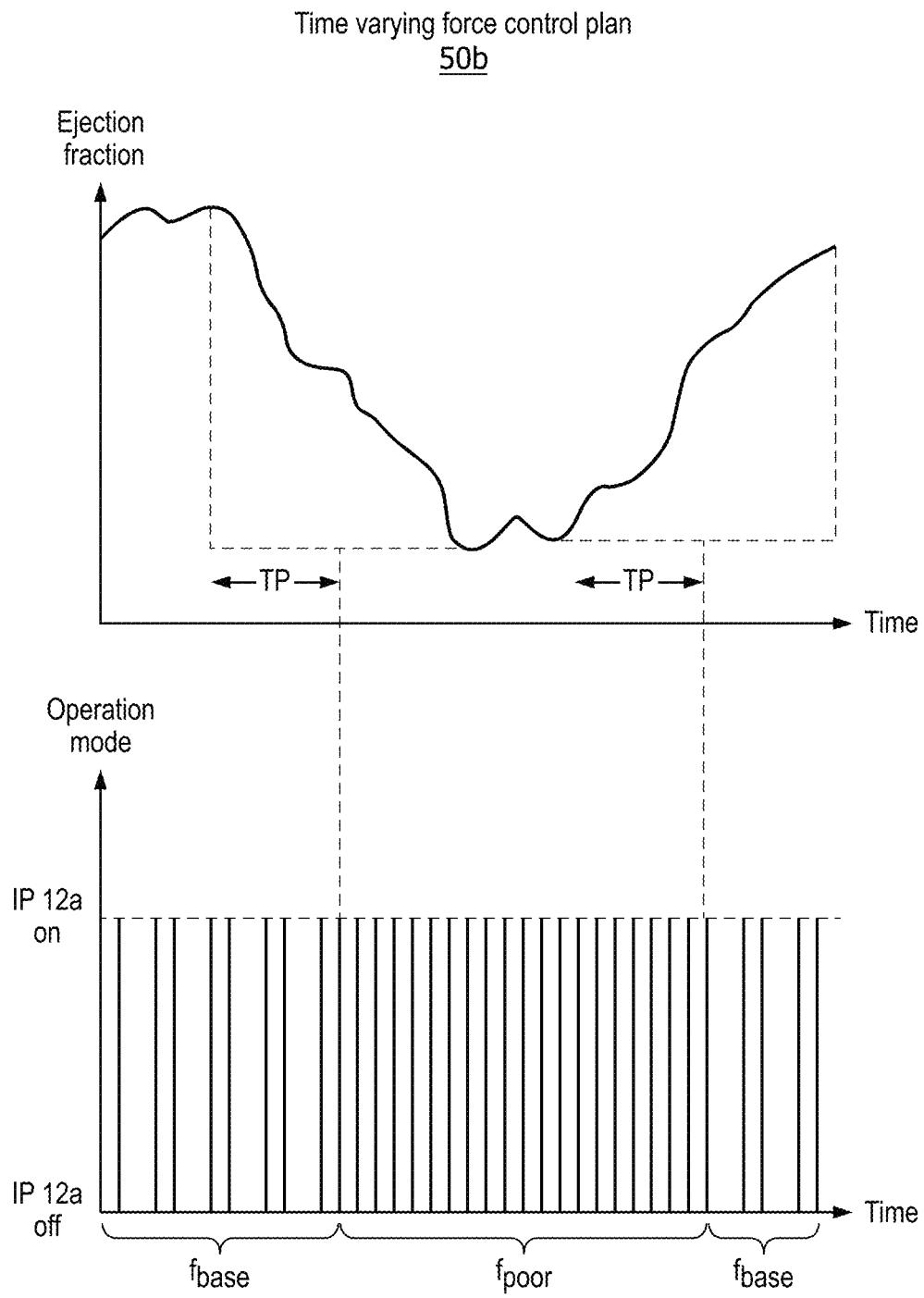

To facilitate a further understanding of the inventions of the present disclosure, the following description of FIGS. 3-4B teaches basic inventive principles of an ultrasound transducer positioning in accordance with the inventive principles of the present disclosure as related to cycling 14a of imaging position 12a and non-imaging position 13a as shown in FIG. 2. From this description of FIGS. 3-4B, those having ordinary skill in the art will appreciate how to apply the inventive principles of the present disclosure to practice numerous and various embodiments of ultrasound transducer positioning in accordance with the inventive principles of the present disclosure.

Generally in practice, an ultrasound transducer positioning of the present disclosure is based on a devising a base time varying force control plan specifying:

1. a base frequency of a forceful positioning of an ultrasound transducer relative to an anatomical structure within an anatomical region;
2. a base duty cycle of a forceful positioning and a forceless positioning of the ultrasound transducer relative to an anatomical structure within an anatomical region;
3. a desired positioning and a desired contact force associated with the forceful positioning of an ultrasound transducer relative to an anatomical structure within an anatomical region;
4. a desired positioning and a desired contact force associated with the forceful positioning of an ultrasound transducer relative to an anatomical structure within an anatomical region;

5. one or more physiological condition of the anatomical region to be extracted from the ultrasound image of the anatomical region; and 6. a delineation of physiological condition(s) of the anatomical region as a definitive indication of any deterioration or any improvement of the physiological condition(s) of the anatomical region.

Referring to FIG. 3, a flowchart 40 is representative of an ultrasound transducer positioning of the present disclosure.

Referring to FIGS. 2 and 3, flowchart 40 is based on a devising of a time varying force control plan specifying a base frequency of imaging position 12a of an ultrasound transducer 20a relative to an anatomical structure within an anatomical region, and a base duty cycle of imaging position 12a and non-imaging position 13a. The devising of the time varying force control plan further specifies a desired positioning and a desired contact force for both imaging position 12a and non-imaging position 13a as will be further described herein.

Flowchart 40 will now be described in the context of imaging position 12a and non-imaging position 13a of ultrasound transducer 20a in the form a TEE probe relative to an inner surface of an esophagus within a thoracic region, and an extraction of an ejection fraction from an ultrasound image of a heart within thoracic region. From the description of flowchart 40, those having ordinary skill in the art will appreciate how to apply flowchart 40 to other forms of ultrasound transducers relative to any anatomical structure within any anatomical region.

Still referring to FIGS. 2 and 3, a stage S42 of flowchart 40 encompasses an initiation of cycling 14a of imaging position 12a and non-imaging position 13a, and a stage S44 of flowchart 40 encompasses a measurement of the ejection fraction of the heart within the thoracic region as extracted from the ultrasound image of a heart within thoracic region.

A stage S46 of flowchart 40 encompasses an adapting of cycling 14a of imaging position 12a and non-imaging position 13a based on the measurement during stage S44 of the ejection fraction of the heart within the thoracic region as extracted from the ultrasound image of a heart within thoracic region. The adaption is in accordance with the time varying force control plan specification a delineation of physiological condition of the ejection fraction of the heart as a definitive indication of any deterioration or any improvement of the ejection fraction of the heart.

Generally in practice, for a definitive indication of any deterioration of the ejection fraction of the heart, the base frequency of imaging position 12a may be increased as symbolically shown in FIG. 3 and/or the base duty cycle may be increased for imaging position 12a as symbolically shown in FIG. 3. As a result, the ultrasound monitoring of the ejection fraction of the heart will be increased for diagnostic purposes.

Conversely in practice, for a definitive indication of any improvement of the ejection fraction of the heart, the base frequency of imaging position 12a may be decreased as symbolically shown in FIG. 3 and/or the base duty cycle may be decreased for imaging position 12a as symbolically shown in FIG. 3. As a result, the ultrasound monitoring of the ejection fraction of the heart will be decreased for diagnostic purposes.

In one exemplary embodiment of stage S46, FIG. 4A illustrates a time varying force control plan 50a delineating a good threshold and a poor threshold as respective definitive indications of an improving or a deteriorating measurement of ejection fraction of the heart. The time varying force control plan 50a further specifies:

1. a good frequency $f_{good}$ and associated duty cycle for imaging position 12a whenever the measurement of the ejection fraction of the heart exceeds the good threshold;

2. a base frequency $f_{base}$ and associated duty cycle for imaging position 12a whenever the measurement of the ejection fraction of the heart is between the good threshold and the poor threshold; and 3. a poor frequency $f_{base}$ and associated duty cycle for imaging position 12a whenever the measurement of the ejection fraction of the heart is below the poor threshold.

As shown in FIG. 4A, the ejection fraction deteriorates from being good to temporarily being poor before showing an improvement toward being good again. As a result, the operation mode of cycling 14a is adapted to the measurement trends of the ejection fraction.

In a second exemplary embodiment of stage S46, FIG. 4B illustrates a time varying force control plan 50b delineating a negative slope and a positive slope over a time period TP threshold as respective definitive indications of an improving or a deteriorating measurement of ejection fraction of the heart. The time varying force control plan 50b further specifies:

1. a transition of a base frequency $f_{base}$ and associated duty cycle for imaging position 12a to a poor frequency $f_{base}$ and associated duty cycle for imaging position 12a whenever the measurement of the ejection fraction of the heart is demonstrating a negative slope over time period TP; and 2. a transition of poor frequency $f_{base}$ and associated duty cycle for imaging position 12a to base frequency $f_{base}$ and associated duty cycle for imaging position 12a whenever the measurement of the ejection fraction of the heart is demonstrating a positive slope over time period TP;

As shown in FIG. 4B, again, the ejection fraction deteriorates from being good to temporarily being poor before showing an improvement toward being good again. As a result, the operation mode of cycling 14a is adapted to the measurement trends of the ejection fraction.

Referring back to FIGS. 2 and 3, stages S44 and S46 are repeated until such time the ultrasound monitoring of the anatomical region is terminated. Those having ordinary skill in the art of the present disclosure will appreciate the benefit of flowchart in minimizing contact between ultrasound transducer 20a and anatomical structure 11 and in minimizing ultrasound expose to anatomical region 10.

To facilitate a further understanding of the inventions of the present disclosure, the following description of FIGS. 5-9B teaches basic inventive principles of an ultrasound transducer positioning system in accordance with the inventive principles of the present disclosure as related to cycling 14a of imaging position 12a and non-imaging position 13a as shown in FIG. 2. From this description of FIGS. 4-9, those having ordinary skill in the art will appreciate how to apply the inventive principles of the present disclosure to practice numerous and various embodiments of ultrasound transducer positioning system in accordance with the inventive principles of the present disclosure.

Figure 5:
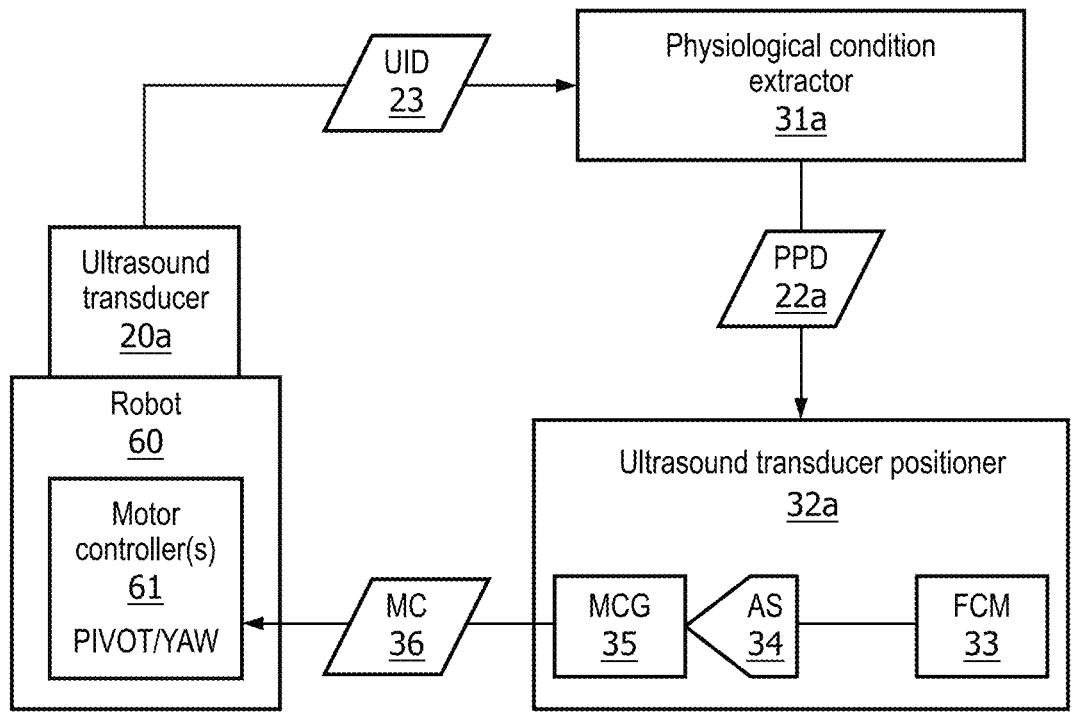
FIG. 5 illustrates an exemplary embodiment of an imaging device positioning system incorporating an ultrasound transducer in accordance with the inventive principles of the present disclosure.

Referring to FIG. 5, an ultrasound transducer positioning system of the present disclosure employs ultrasound transducer 20a and an ultrasound probe robot 60.

In practice, ultrasound transducer 20a may include any type of transducer array as known in the art of the present disclosure and hereinafter conceived including, but not limited to, a linear array, a phased array, a curvi-linear array and a matrix sensor array.

Figure 6:
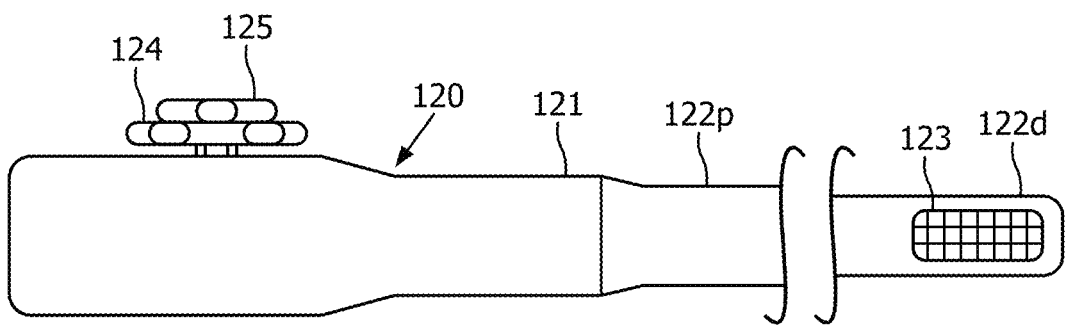
FIG. 6 illustrates an exemplary embodiment of an ultrasound transducer as known in the art.

In one embodiment of ultrasound transducer 20a, FIG. 6 illustrates a TEE probe 120 as known in the art employing a handle 121 and an elongated probe having a proximal end 122p attached to handle 121 and a distal head end 122d with an ultrasound transducer array 123. TEE probe 120 further employs a yaw actuation dial 124 for adjusting a yaw degree freedom of ultrasound transducer array 123, and a pitch actuation dial 125 for adjusting a pitch degree freedom of ultrasound transducer array 123.

Referring back to FIG. 5, in practice, ultrasound probe robot 60 may be any type of robot, as known in the art of the present disclosure and hereinafter conceived, employing one or more motor controller(s) 61 for controlling a yawing and/or a pitching of an ultrasound transducer array of ultrasound transducer 20a. Motor controllers 61 may also be utilized to control a rolling and/or a translation of the ultrasound transducer array of ultrasound transducer 20a.

Figure 7:
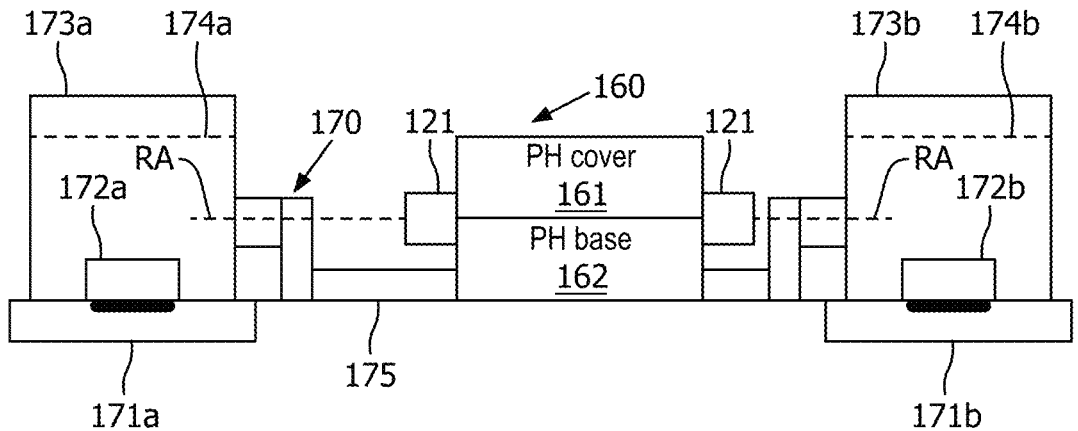
FIG. 7 illustrates an exemplary embodiment of an ultrasound probe robot as known in the art.

In one embodiment of ultrasound probe robot 60, FIG. 7 illustrates an ultrasound probe robot including a robotic actuator 160 and an actuator platform 170.

Robotic actuator 160 employs a probe handle cover 133 having a concave inner surface (not shown) and a probe handle base 135 having a concave inner surface (not shown) for defining a actuation chamber upon being magnetically coupled via one or more magnetic couplers (not shown). In operation, the chamber houses the actuation dials 124 and 125 of TEE probe 120 (FIG. 6) and the magnetic coupling provides an advantage of facilitating an easy removal of TEE probe 120 is desired, particularly if operating circumstance dictate manual control of TEE probe 120.

Robotic actuator 160 further employs a motor (not shown) and a motor controller (not shown) yielding motorized gears controllable by ultrasound transducer positioner 32a via an electrical coupling of robotic controller 60 to the motor controllers. In operation, the motorized gears are sufficient to engage and rotate actuation dials 124 and 125 of TEE probe 120 for a desired pitching and/or yawing of transducer array 123.

Actuator platform 170 provides an additional two (2) degrees for freedom of lateral motion and rotational motion for transducer array 123, which is capable of being pitched and/or yawed by robotic actuator 160 as previously described herein.

To this end, actuator platform 170 employs a pair of rails 171, a pair of sliders 162, a pair of rotation motors 163, and a crank shaft 1745. By techniques known in the art, sliders 162 are slidably coupled to rails 171 and affixed to rotation motors 163, and crank shaft 175 is rotatably coupled to rotation motors 163. In operation, a ultrasound transducer positioner 32a (FIG. 5) controls a laterally movement of crank shaft 175 via conventional control of a sliding of sliders 162 along rails 171 and for revolving crank shaft 175 about a rotational axis RA via a control of rotation motors 163 (In practice, rotation motors 163 may have groves 174 for supporting a portion of handle 121 of TEE probe 120, TEE probe 120 itself, and/or cabling of the TEE probe 120.

Referring back to FIG. 5, the ultrasound transducer positioning system of the present disclosure further employs ultrasound transducer controller 30a (FIG. 2), of which physiological condition extractor 31a and ultrasound transducer positioner 32a are shown.

In practice, ultrasound transducer controller 30a may embody any arrangement of hardware, software, firmware and/or electronic circuitry for a positioning of ultrasound transducer 20a internal to or external to anatomical region 10.

In one embodiment ultrasound transducer controller 30a may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a display, a mouse, and a keyboard for receiving user commands. In some embodiments, the user interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules 31a and 32a in the form of executable software/firmware.

More particularly, still referring to FIG. 5, physiological parameter extractor 31a consists of executable software/firmware for generating physiological parameter data 22a being informative of one or more physiological conditions of anatomical region 10 (FIG. 2) extracted from the ultrasound image of the anatomical region as previously described herein in connection with the description of FIGS. 2-4B.

Ultrasound transducer positioner 32a employs routines in the form of a force control manager 33 and a motor command generator 35.

Force control manager 33 consists of executable software/firmware for generating an enable signal 34 for switching motor command generator 35 between an ON mode for forceful positioning and an OFF mode for forceful positioning as previously described herein in connection with the description of FIGS. 2-4B. Force control manager 33 further adapts the generation of enable signal 34 to the physiological condition(s) of the anatomical region indicated by physiological parameter data 22a as previously described herein in connection with the description of FIGS. 2-4B.

Motor command generator 35 consists of executable software/firmware for generating motor commands 36 for controlling a yawing and/or a pitching of the transducer array by motor controller(s) 61 in accordance within enable signal 34.

Figure 8A:
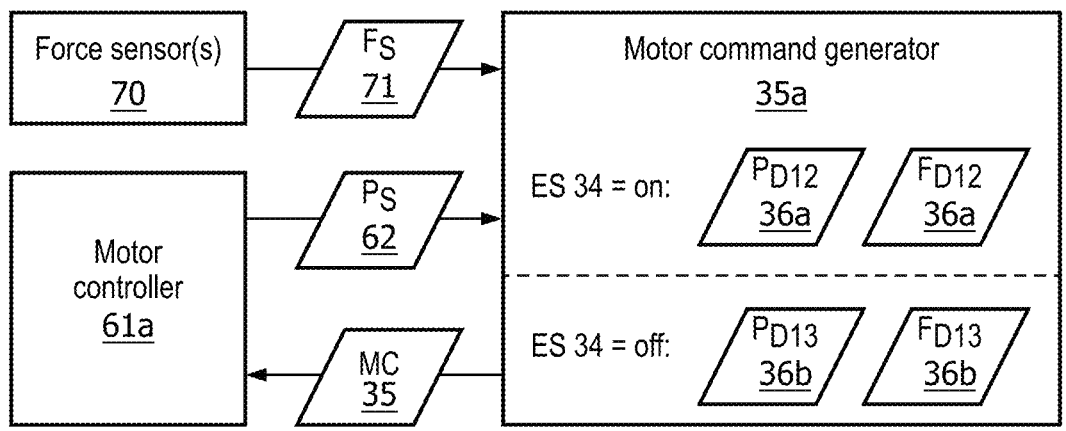
FIGS. 8A and 8B illustrates an exemplary embodiment of a sensed force/position control by a motor command generator in accordance with the inventive principles of the present disclosure.

In one embodiment of motor command generator 35, FIG. 8A illustrates a motor controller 61a communicating a position signal 62 to a motor command generator 35a with the position signal 62 being indicative of a yaw position and/or a pitch position of the transducer array (FIG. 5). Also shown is one more force sensors 70 communicating force signal(s) 71 to motor command generator 35a with each force signal 71 being indicative of a contact force between ultrasound transducer 20a and an anatomical structure of anatomical region 10 (FIG. 2).

In practice, force sensors 70 may be embedded in ultrasound transducer 20a and/or ultrasound probe robot 60.

Still referring to FIG. 8A, motor command generator 35a stores a desired positioning 36a and a desired contact force 36a of the transducer array applicable to an ON mode of enable signal 34, and a desired positioning 36b and a desired contact force 36b of the transducer array applicable to an OFF mode of enable signal 34. Upon an actuation position calibration and a contract force calibration of the ultrasound transducer array of ultrasound transducer 20a as known in the art of the present disclosure, motor command generator 35a generates motor command 36 from an execution of a sensed force control scheme 80 of a simultaneous actuation position and contact force control as shown in FIG. 8B.

Figure 8B:
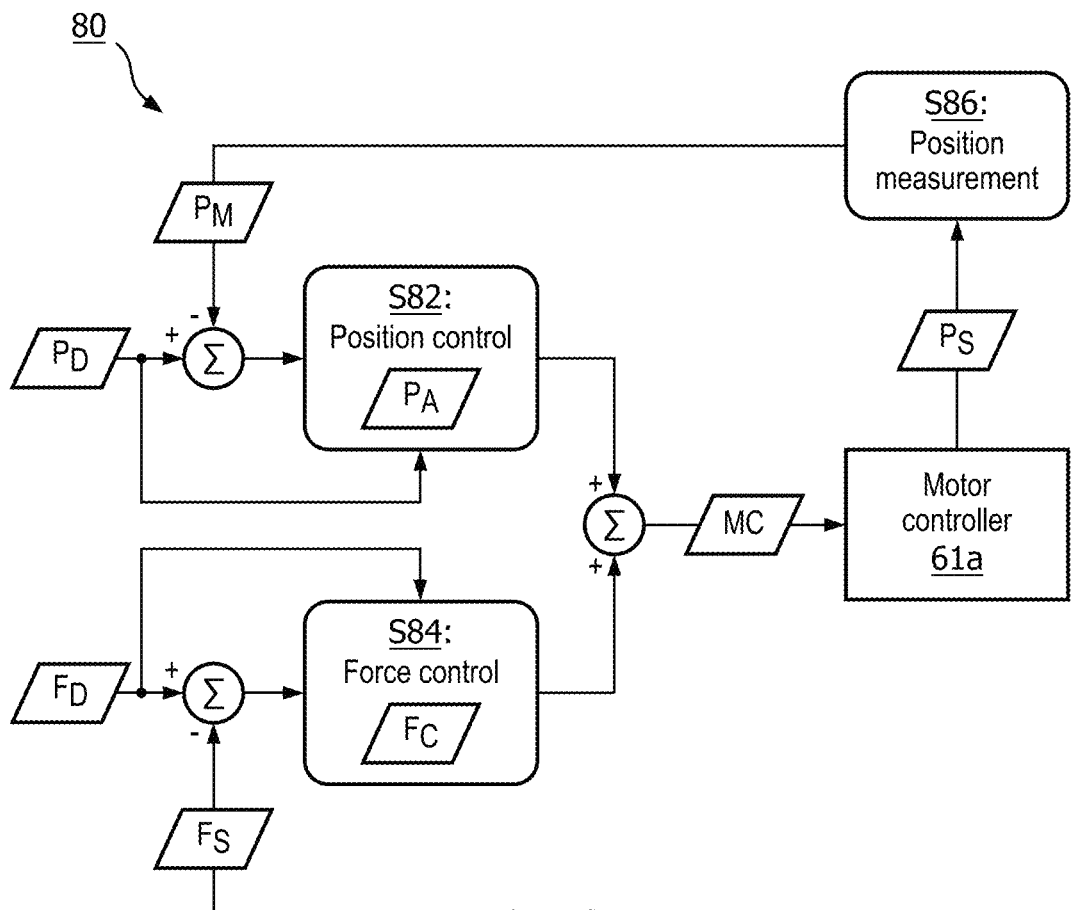

Referring to FIG. 8B, a generation of motor commands 36 involves an application of contact force correction $F_C$ to an actuation position $P_A$ in view of minimizing a position error between desired actuation position $P_D$ and a measured motor position $P_M$, and a contract force error between contact force correction $F_C$ and an sensed contact force $F_S$.

Specifically, motor controller 61a continually communicates a sensed motor position $P_S$ during a stage S86 of scheme 80 to motor command generator 35a. In response thereto, motor command generator 35a periodically measures sensed motor positions $P_S$ and compares the measured motor positions $P_M$ to motor positions associated with a desired actuation position $P_D$ of the head of TEE probe 120 and the resulting position error is an input for position control stage S82 designed to minimize the position error. In practice, motor command generator 35a may execute any control technique(s) as known in the art for minimizing the position error (e.g., a PID control).

Motor command generator 35a also compares the sensed force signal $F_S$ to a desired contact force FD and the resulting contact force error is an input for a force control stage S82 designed to minimize the contact force error. In practice, motor command generator 35a may execute any control technique(s) as known in the art for minimizing the contact force error (e.g., a PID control).

A direct method for generating motor command MC is derived from a model that assumes that contact surface of the transducer array acts as an ideal spring, in which case:

$$\Delta f = K(x - xo)$$

where $\Delta f$ is the force error signal, x is the position of the contact point, xo would be the position of TEE probe 40 if there was no obstacle, and K is elastic constant of the anatomical structure (values known in literature can be used). Since xo can be known from the kinematic model of TEE probe 40, there is a direct link between motor commands and the force. Similarly to position control value:

$$x = \frac{\Delta f}{K} + x0$$

Motor command generator 35a will continually loop through the stages of scheme 80 during the procedure.

Figure 9A:
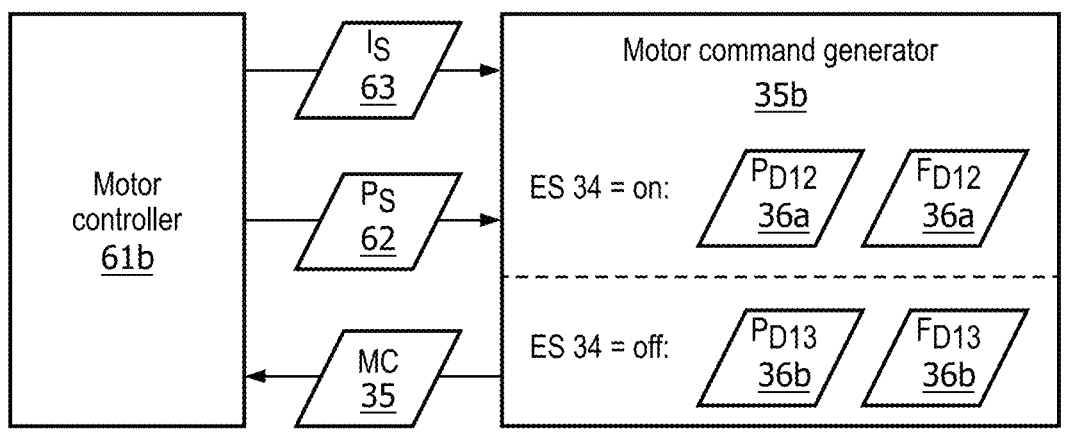
FIGS. 9A and 9B illustrates an exemplary embodiment of a sensorless force/position control by a motor command generator in accordance with the inventive principles of the present disclosure.

In a second embodiment of motor command generator 35, FIG. 9A illustrates a motor controller 61b communicating a position signal 62 and a motor current signal 63 to a motor command generator 35b with the position signal 62 being indicative of a yaw position and/or a pitch position of the transducer array of ultrasound transducer 20a (FIG. 5) and motor current signal 63 being indicative of currents applied by motor controller 61b to motors for the current positioning of the transducer array.

Still referring to FIG. 9A, motor command generator 35b also stores desired positioning 36a and desired contact force 36a of the transducer array applicable to an ON mode of enable signal 34, and desired positioning 36b and desired contact force 36b of the transducer array applicable to an OFF mode of enable signal 34. Upon an actuation position calibration and a contract force calibration of the transducer array as known in the art of the present disclosure, motor command generator 35b generates motor command 36 from an execution of a sensed force control scheme 90 of a simultaneous actuation position and contact force control as shown in FIG. 9B.

Figure 9B:
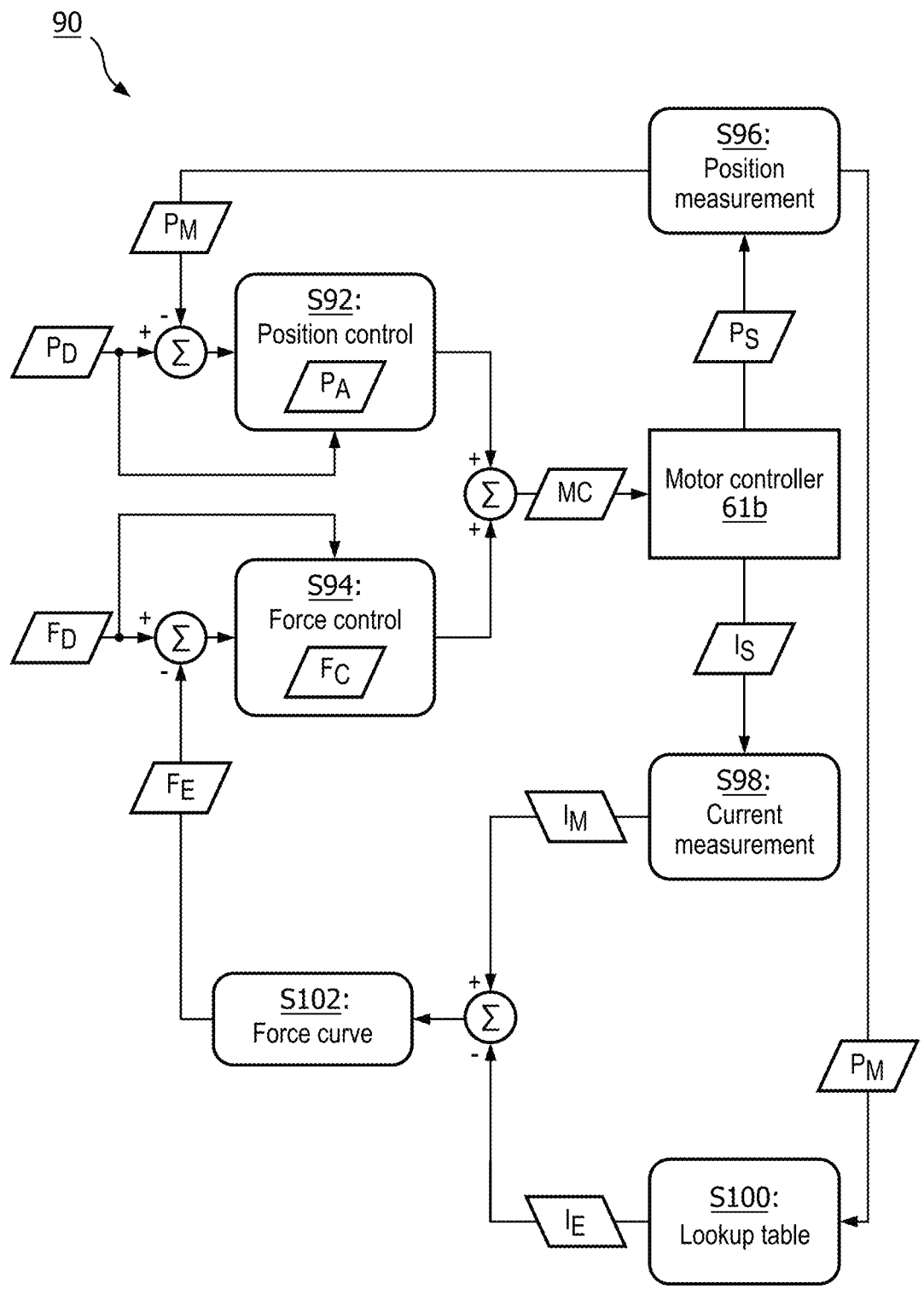

Referring to FIG. 9B, a generation of motor commands 36 involves an application of contact force correction $F_C$ to an actuation position $P_A$ in view of minimizing a position error between desired actuation position $P_D$ and a measured motor position $P_M$, and a contract force error between contact force correction $F_C$ and a sensed contact force $F_S$.

Specifically, motor controller 61b continually communicates a sensed motor position $P_S$ during a stage S96 of scheme 90 to motor command generator 35b. In response thereto, motor command generator 35b periodically measures sensed motor positions $P_S$ and compares the measured motor positions $P_M$ to motor positions associated with a desired actuation position $P_D$ of the head of TEE probe 120 and the resulting position error is an input for position control stage S92 designed to minimize the position error. In practice, motor command generator 35b may execute any control technique(s) as known in the art for minimizing the position error (e.g., a PID control).

Motor command generator 35b also periodically in sync measures sensed motor currents $I_S$ and combines the measured sensed motor currents $I_S$ to an expected motor currents $I_E$, which is calculated by inputting measured motor positions $P_M$ into the lookup table of stage S100 as obtained during a calibrations. The lookup table takes two inputs of position of the two dials and returns two expected current values $I_E$ for each degree-of-freedom. During stage S102 expected current values IF and the measured motor current values IM are current fed to force curve (C→F) computed during calibration to estimate an expected contact force FE on the head of TEE probe 120.

Motor command generator 35b compares the expected force signal FE to a desired contact force FD and the resulting contact force error is an input for a force control stage S94 designed to minimize the contact force error. In practice, motor command generator 35b may execute any control technique(s) as known in the art for minimizing the contact force error (e.g., a PID control).

Again, a direct method for generating motor command MC is derived from a model that assumes that contact surface of the transducer array acts as an ideal spring, in which case:

$$\Delta f = K(x - xo)$$

where $\Delta f$ is the force error signal, x is the position of the contact point, xo would be the position of TEE probe 40 if there was no obstacle, and K is elastic constant of the anatomical structure (values known in literature can be used). Since xo can be known from the kinematic model of TEE probe 40, there is a direct link between motor commands and the force. Similarly to position control value:

$$x = \frac{\Delta f}{K} + x0$$

Motor command generator 35b will continually loop through the stages of scheme 90 during the procedure.

Referring back to FIGS. 2 and 5, in practice, ultrasound transducer controller 30a may be structurally implemented as a stand-alone controller or installed within a workstation, tablet, server, etc.

Figure 10:
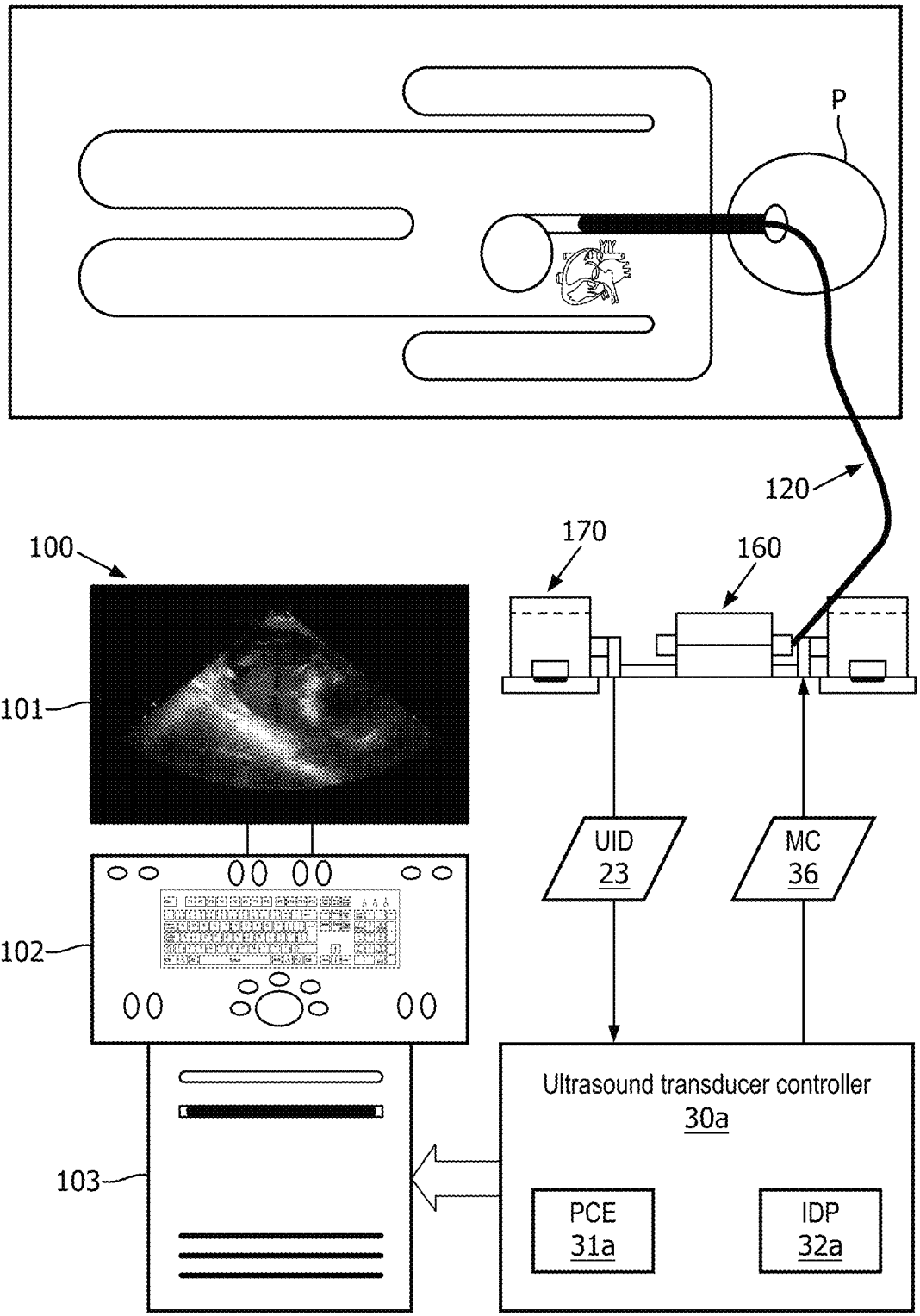
FIG. 10 illustrates an exemplary embodiment of the imaging device positioning system of FIG. 5 in accordance with the inventive principles of the present disclosure.

In one embodiment, FIG. 10 illustrates a workstation 100 having a monitor 101, a keyboard 102 and a computer 103 having ultrasound transducer controller 30a installed therein. For this exemplary embodiment, TEE probe 120 is supported by robotic actuator 160 and actuator platform 170 as previously described herein for insertion of the distal end within an esophagus of a patient P.

In practice, ultrasound transducer controller 30a may further employ an application for activating and deactivating the imaging capability of TEE probe 120 as known in the art of the present disclosure or such an application may be separately installed on computer 103 or another workstation, tablet, server, etc.

Also in practice, ultrasound transducer controller 30a may further employ an application for displaying an ultrasound image on monitor 101 as known in the art of the present disclosure or such an application may be separately installed on computer 103 or another workstation, tablet, server, etc.

Further in practice, in lieu of receiving ultrasound imaging data 23 from ultrasound transducer 30a, ultrasound transducer controller 30a may receive ultrasound display data informative of the display of the ultrasound image on monitor 101 whereby ultrasound transducer controller 30a extracts the physiological conditions(s) from the ultrasound display data.

Figure 11:
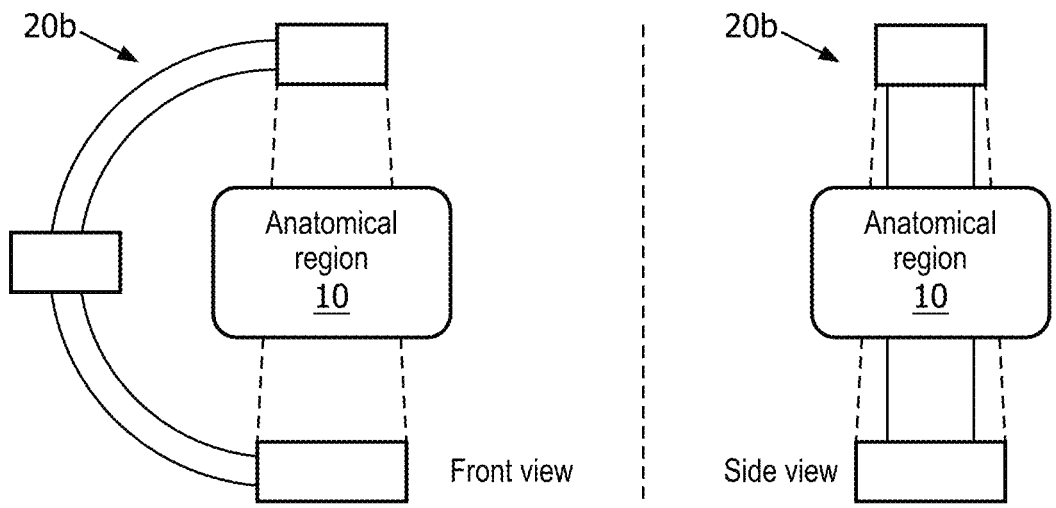
FIG. 11 illustrates an exemplary positioning of an X-ray gantry external to an anatomical region in accordance with the inventive principles of the present disclosure.
Figure 11:
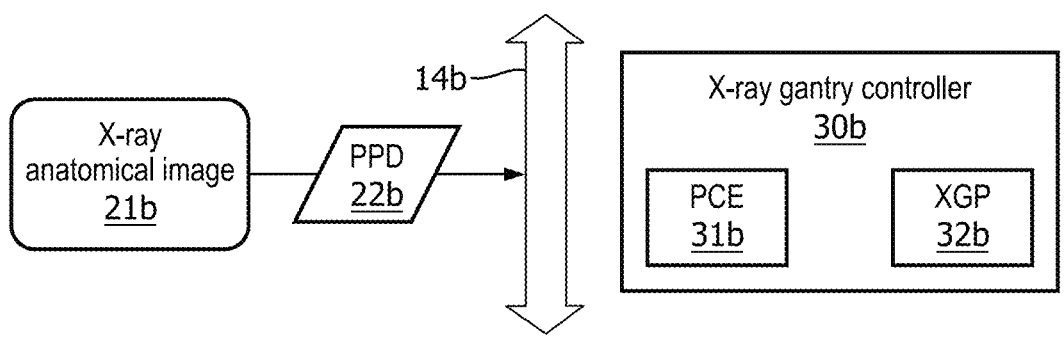
Figure 11:
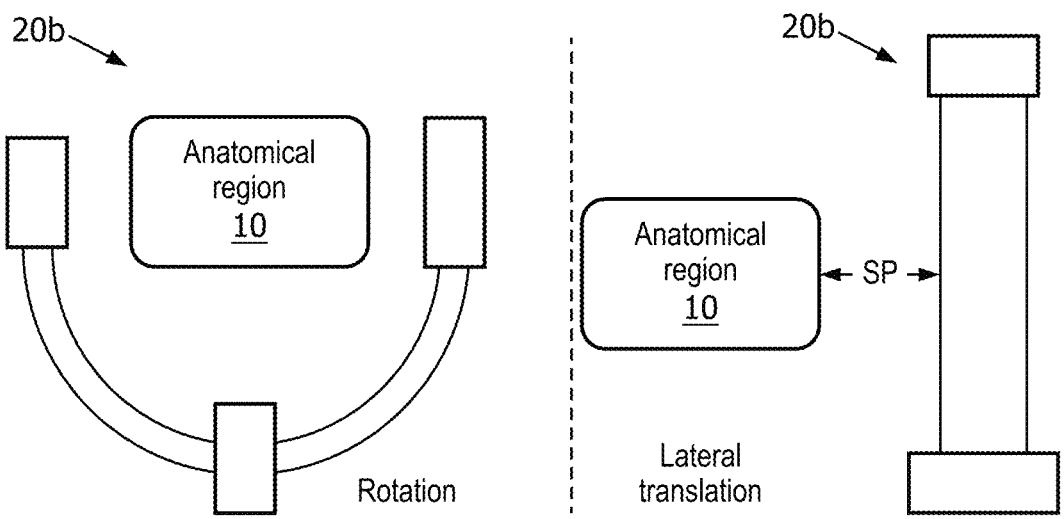
Figure 12:
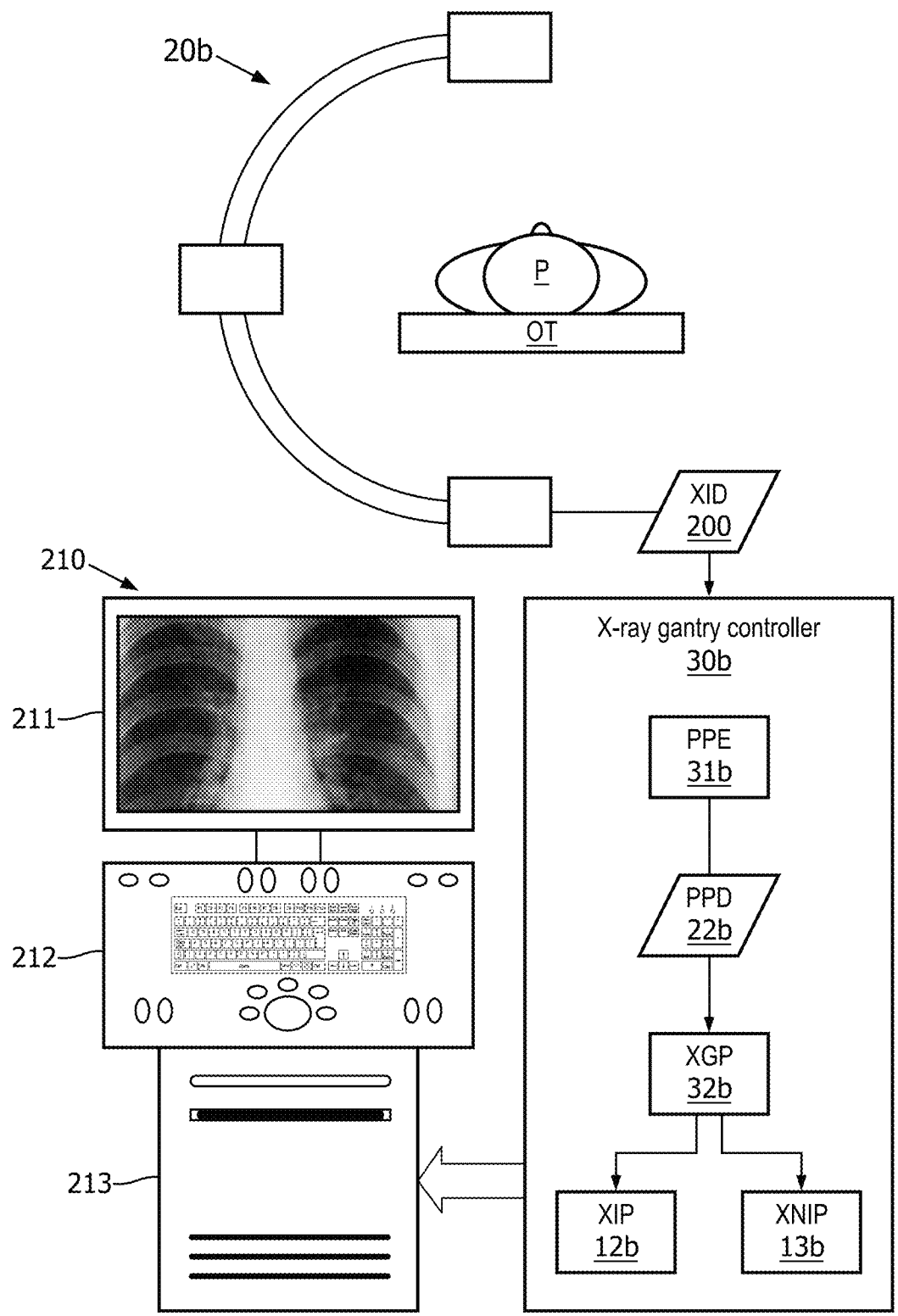
FIG. 12 illustrates an exemplary embodiment of an imaging device positioning system incorporating an X-ray gantry in accordance with the inventive principles of the present disclosure.

To facilitate a further understanding of the inventions of the present disclosure, the following description of FIGS. 11 and 12 teaches basic inventive principles of a positioning of an X-ray gantry encircling an anatomical region in accordance with the inventive principles of the present disclosure. From this description of FIGS. 11 and 12, those having ordinary skill in the art will appreciate how to apply the inventive principles of the present disclosure to practice numerous and various embodiments of positioning of an X-ray gantry encircling an anatomical region in accordance with the inventive principles of the present disclosure.

Referring to FIG. 11, an imaging position 12b of the present disclosure encompasses a positioning of an X-ray gantry 20b to encircle anatomical region 10 at an orientation whereby an imaging capability X-ray gantry 20b as known in the art of the present disclosure is activated as exemplarily symbolized by the dashed lines to generate an X-ray anatomical image 21b.

Conversely, a non-imaging position 13b of the present disclosure encompasses a positioning of X-ray gantry 20b whereby the imaging capability of X-ray gantry 20b is deactivated. Non-imaging position 13b may involve a rotation of X-ray gantry 20b at an orientation incapable of properly imaging anatomical region 10 and/or a lateral translation to create a spacing SP between anatomical region 10 and X-ray gantry 20b.

Still referring to FIG. 11, a periodic or irregular cycling 14b of X-ray gantry 20b between imaging position 12b and non-imaging position 13b involves a cyclical arrangement of imaging position 12b and non-imaging position 13b at a fixed or variable frequency and/or a fixed or variable duty cycle for purposes of visually monitoring a specific aspect of anatomical region 10 while minimizing any exposure of anatomical region 10 to any radiation/energy emitted by X-ray gantry 20b for purposes of imaging anatomical region 10.

To this end, an X-ray gantry controller 30b employs a physiological condition extractor 31b for extracting physiological parameter data 22b from X-ray anatomical image 21b of the anatomical region 10 generated by X-ray gantry 20b whereby physiological parameter data 22b is informative of one or more physiological conditions of anatomical region 10 as will be further explained herein. For example, if anatomical region 10 is a thoracic region, then the physiological condition(s) of the thoracic region may be an ejection fraction, a stroke volume, a cardiac output, an IVC/SVC diameter for fluid status and/or a Doppler flow to an organ.

In practice, as would be appreciated by those having ordinary skill in the art of the present disclosure, any extraction technique known in the art may be implemented in dependence upon the type of physiological condition(s) being extracted from X-ray anatomical image 21b of the anatomical region 10.

X-ray gantry controller 30b further employs an X-ray gantry positioner 32b for controlling an adaption of cycling 14b of a positioning of X-ray gantry 20b to the physiological condition(s) of anatomical region 10 extracted from X-ray anatomical image 21b of the anatomical region 10. In practice, the adaption of cycling 14b of a positioning of X-ray gantry 20b may include an increase to the fixed/variable frequency and/or the fixed/variable duty cycle of imaging position 12b in view of any deterioration of the physiological condition(s) of the anatomical region as delineated in the physiological parameter data 22b, or conversely a decrease to the fixed/variable frequency and/or the fixed/variable duty cycle of imaging position 12b in view of any improvement of the physiological condition(s) of the anatomical region as delineated in the physiological parameter data 22b.

Generally, any deterioration or any improvement of the physiological condition(s) of the anatomical region may be delineated in the physiological parameter data 22b by any technique providing a definitive indication of such deterioration or improvement as known in the art of the present disclosure. More particularly in practice, any deterioration or any improvement of the physiological condition(s) of the anatomical region may be delineated by one or more thresholds established relative to the physiological parameter data 22b as previously described herein. Concurrently or alternatively in practice, any deterioration or any improvement of the physiological condition(s) of the anatomical region may be delineated by a negative slope or a positive slope of the physiological parameter data 22b over a specified time period as will be further described herein.

Still referring to FIG. 11, in practice, X-ray gantry controller 30b may be structurally implemented as a stand-alone controller or installed within a workstation, tablet, server, etc.

In one embodiment, FIG. 12 illustrates a workstation 210 having a monitor 211, a keyboard 212 and a computer 213 having X-ray gantry controller 30b installed therein.

In practice, X-ray gantry controller 30b may embody any arrangement of hardware, software, firmware and/or electronic circuitry for a positioning of X-ray gantry 20b encircling anatomical region 10.

In one embodiment X-ray gantry controller 30b may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a display, a mouse, and a keyboard for receiving user commands. In some embodiments, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules 31b and 32b in the form of executable software/firmware.

More particularly, still referring to FIG. 12, physiological parameter extractor 31b consists of executable software/firmware for generating physiological parameter data 22b being informative of one or more physiological conditions of anatomical region 10 (FIG. 2) extracted from the X-ray image 21b of the anatomical region 10 as previously described herein in connection with the description of FIG. 11.

X-ray gantry positioner 32b consists of executable software/firmware for adapting a cycling 14a of X-ray gantry 20b between imaging position 12b and non-imaging position 13b to the physiological conditions of anatomical region 10 extracted from the X-ray image 21b of the anatomical region 10 as previously described herein in connection with the description of FIG. 11.

In practice, X-ray gantry controller 30b may further employ an application for activating and deactivating the imaging capability of X-ray gantry 20b for generating X-ray imaging data 200 as known in the art of the present disclosure or such an application may be separately installed on computer 213 or another workstation, tablet, server, etc.

Also in practice, X-ray gantry controller 30b may further employ an application for displaying an X-ray image on monitor 211 as known in the art of the present disclosure or such an application may be separately installed on computer 213 or another workstation, tablet, server, etc.

Further in practice, in lieu of receiving X-ray imaging data 220 from X-ray gantry 20b, X-ray gantry controller 30b may receive X-ray display data informative of the display of the X-ray image on monitor 213 whereby physiological parameter extractor 31b extracts the physiological conditions(s) from the X-ray display data.

Figure 13:
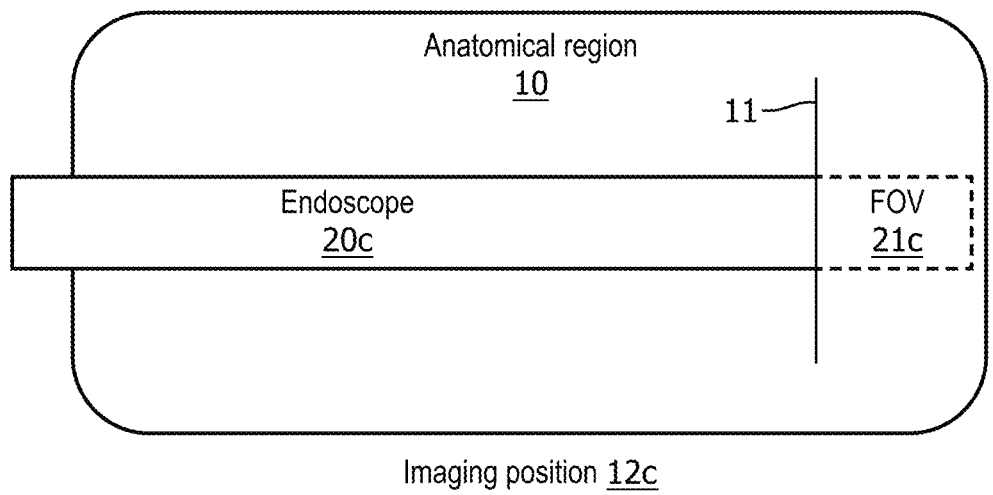
FIG. 13 illustrates an exemplary positioning of a scope external to an anatomical region in accordance with the inventive principles of the present disclosure.
Figure 13:
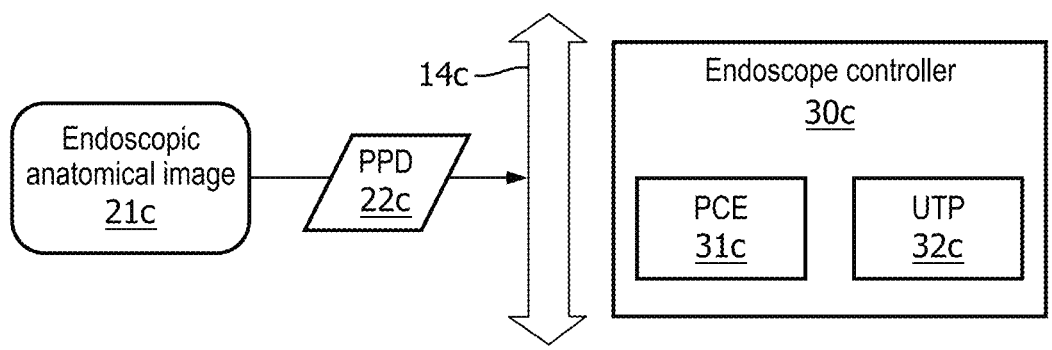
Figure 13:
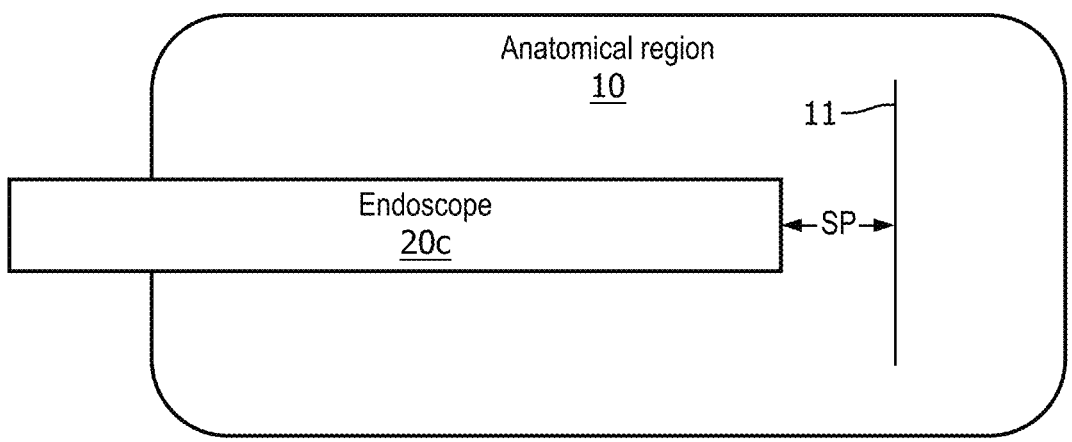
Figure 14:
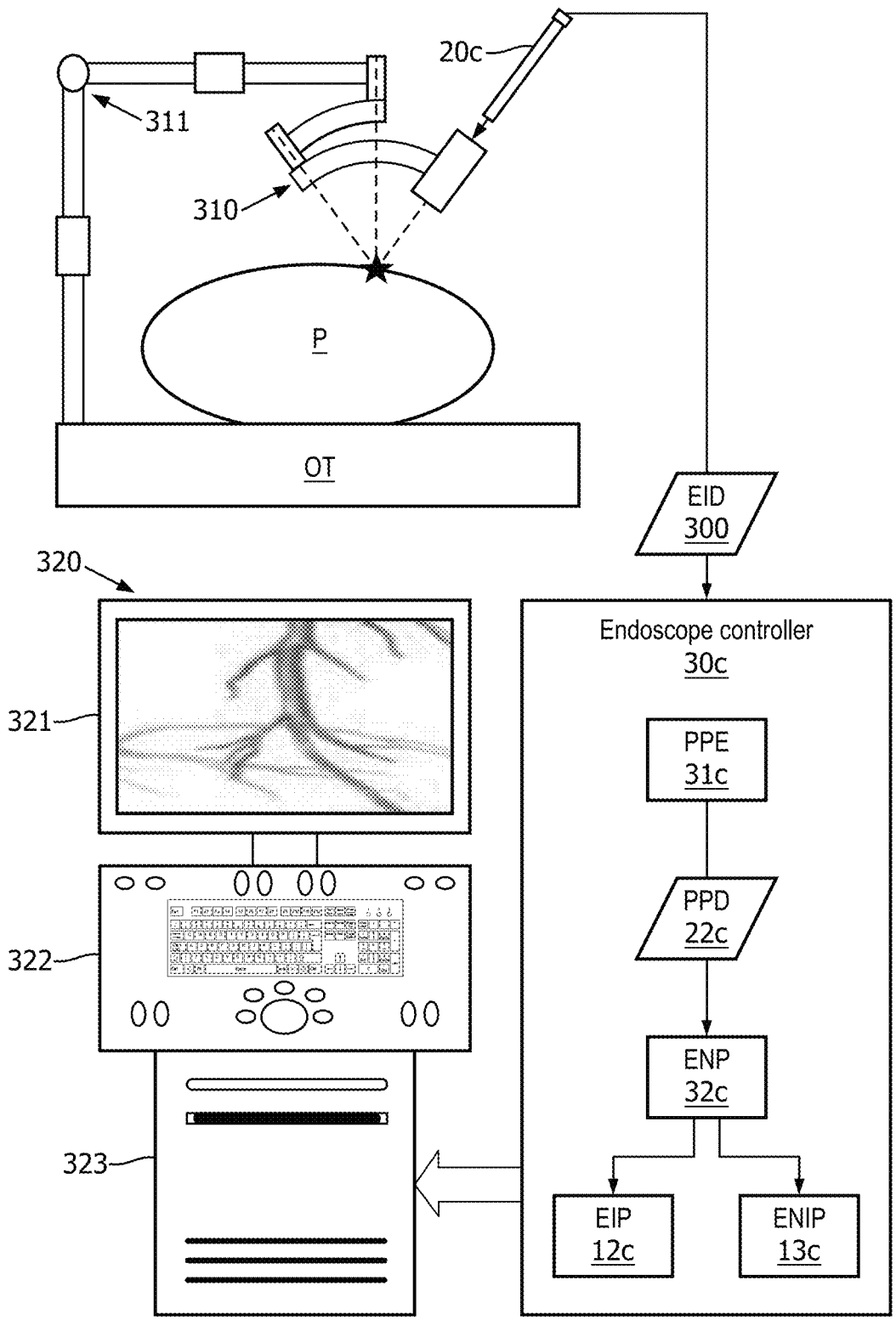
FIG. 14 illustrates an exemplary embodiment of an imaging device positioning system incorporating a scope in accordance with the inventive principles of the present disclosure.

To facilitate a further understanding of the inventions of the present disclosure, the following description of FIGS. 13 and 14 teaches basic inventive principles of a positioning of an endoscope inserted through a port into an anatomical region in accordance with the inventive principles of the present disclosure. From this description of FIGS. 13 and 14, those having ordinary skill in the art will appreciate how to apply the inventive principles of the present disclosure to practice numerous and various embodiments of positioning of an endoscope inserted through a port into an anatomical region in accordance with the inventive principles of the present disclosure.

Referring to FIG. 13, an imaging position 12c of the present disclosure encompasses a positioning of an endoscope 20c inserted through a port into anatomical region 10 in direct contact with an anatomical structure 11 whereby an imaging capability of endoscope 20c as known in the art of the present disclosure is activated as exemplarily symbolized by field of view 21c to generate an endoscopic anatomical image 21c.

Conversely, a non-imaging position 13c of the present disclosure encompasses a positioning of endoscope 20c inserted through a port into whereby the imaging capability of endoscope 20c is deactivated. Non-imaging position 13c may involve a pivoting of endoscope 20c away from anatomical structure 11 within anatomical region and/or a partial or full withdrawal of endoscope 20c from anatomical region 10 to create a spacing SP between anatomical structure 11 and endoscope 20c.

Still referring to FIG. 13, a periodic or irregular cycling 14c of endoscope 20c between imaging position 12c and non-imaging position 13c involves a cyclical arrangement of imaging position 12c and non-imaging position 13c at a fixed or variable frequency and/or a fixed or variable duty cycle for purposes of visually monitoring a specific aspect of anatomical region 10 while minimizing contact between anatomical structure 11 and endoscope 20c.

To this end, an endoscope controller 30c employs a physiological condition extractor 31c for extracting physiological parameter data 22c from endoscopic anatomical image 21c of the anatomical region 10 generated by endoscope 20c whereby physiological parameter data 22c is informative of one or more physiological conditions of anatomical region 10 as will be further explained herein. For example, if anatomical region 10 is a thoracic region, then the physiological condition(s) of the thoracic region may be an ejection fraction, a stroke volume, a cardiac output, an IVC/SVC diameter for fluid status and/or a Doppler flow to an organ.

In practice, as would be appreciated by those having ordinary skill in the art of the present disclosure, any extraction technique known in the art may be implemented in dependence upon the type of physiological condition(s) being extracted from endoscopic anatomical image 21c of the anatomical region 10.

Endoscope controller 30c further employs an endoscope positioner 32c for controlling an adaption of cycling 14c of a positioning of endoscope 20c to the physiological condition(s) of anatomical region 10 extracted from endoscopic anatomical image 21c of the anatomical region 10. In practice, the adaption of cycling 14c of a positioning of endoscope 20c may include an increase to the fixed/variable frequency and/or the fixed/variable duty cycle of imaging position 12c in view of any deterioration of the physiological condition(s) of the anatomical region as delineated in the physiological parameter data 22c, or conversely a decrease to the fixed/variable frequency and/or the fixed/variable duty cycle of imaging position 12c in view of any improvement of the physiological condition(s) of the anatomical region as delineated in the physiological parameter data 22c.

Concurrently or alternatively in practice, the adaption of cycling 14a may include an increase to a degree of contact force between ultrasound transducer 20a and an anatomical structure of anatomical region 10 in view of any deterioration of the physiological condition(s) of the anatomical region as delineated in the physiological parameter data 22a to thereby facilitate a higher quality of imaging of anatomical region 10, or conversely a decrease to a degree of contact force between ultrasound transducer 20a and an anatomical structure of anatomical region 10 in view of any improvement of the physiological condition(s) of the anatomical region as delineated in the physiological parameter data 22a to thereby facilitates an acceptable quality of imaging of anatomical region 10 at a lesser degree of contact.

Generally, any deterioration or any improvement of the physiological condition(s) of the anatomical region may be delineated in the physiological parameter data 22c by any technique providing a definitive indication of such deterioration or improvement as known in the art of the present disclosure. More particularly in practice, any deterioration or any improvement of the physiological condition(s) of the anatomical region may be delineated by one or more thresholds established relative to the physiological parameter data 22c as previously described herein. Concurrently or alternatively in practice, any deterioration or any improvement of the physiological condition(s) of the anatomical region may be delineated by a negative slope or a positive slope of the physiological parameter data 22c over a specified time period as will be further described herein.

Still referring to FIG. 13, in practice, endoscope controller 30c may be structurally implemented as a stand-alone controller or installed within a workstation, tablet, server, etc.

In one embodiment, FIG. 14 illustrates a workstation 320 having a monitor 321, a keyboard 322 and a computer 323 having endoscope controller 30c installed therein.

In practice, endoscope controller 30c may embody any arrangement of hardware, software, firmware and/or electronic circuitry for a positioning of endoscope 20c through the port into anatomical region 10.

In one embodiment endoscope controller 30c may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a display, a mouse, and a keyboard for receiving user commands. In some embodiments, the user interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules 31c and 32c in the form of executable software/firmware.

More particularly, still referring to FIG. 14, physiological parameter extractor 31c consists of executable software/firmware for generating physiological parameter data 22c being informative of one or more physiological conditions of anatomical region 10 (FIG. 2) extracted from the endoscopic anatomical image 21c of the anatomical region 10 as previously described herein in connection with the description of FIG. 13.

Endoscope positioner 32c consists of executable software/firmware for adapting a cycling 14a of endoscope 20c between imaging position 12c and non-imaging position 13c to the physiological condition(s) of anatomical region 10 extracted from the endoscopic anatomical image 21c of the anatomical region 10 as previously described herein in connection with the description of FIG. 13.

More particularly, endoscope positioner 32c controls an actuation of an endoscope robot 310 and/or robot platform 311 as known in the art of the present disclosure to translate, rotate and/or pivot endoscope 20c between imaging position 12c and non-imaging position 13c based on the physiological condition(s) of anatomical region 10 extracted from the endoscopic anatomical image 21c of the anatomical region 10

In practice, endoscope controller 30c may further employ an application for activating and deactivating the imaging capability of endoscope 20c for generating endoscope imaging data 300 as known in the art of the present disclosure or such an application may be separately installed on computer 213 or another workstation, tablet, server, etc.

Also in practice, endoscope controller 30c may further employ an application for displaying an endoscopic image on monitor 32 as known in the art of the present disclosure or such an application may be separately installed on computer 323 or another workstation, tablet, server, etc.

Further in practice, in lieu of receiving endoscope imaging data 300 from endoscope 20c, endoscope controller 30c may receive endoscope display data informative of the display of the endoscopic image on monitor 323 whereby physiological parameter extractor 31c extracts the physiological conditions(s) from the endoscope display data.

Referring to FIGS. 1-14, those having ordinary skill in the art will appreciate numerous benefits of the present disclosure including, but not limited to, an improvement over ultrasound monitoring systems and methods by the inventions of the present disclosure in providing a controlled ultrasound image acquisition of anatomical region based on physiological parameters extracted from the anatomical images whereby sufficient information about a patient's condition is obtainable without any unnecessary contact between the patient and the imaging device and/or without any excessive exposure of the patient to an imaging radiation/energy projected by the imaging device.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive imaging device positioning systems and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A system for positioning an imaging device, the system comprising:
   the imaging device configured to generate an image of an anatomical region;
   a controller configured to control the positioning of the imaging device relative to the anatomical region, the controller configured to:
      in response to generation of the image of the anatomical region, extract a physiological condition of the anatomical region from the image of the anatomical region, and
      adapt cycling of the positioning of the imaging device between a position with imaging functionality of the imaging device activated and a position with the imaging functionality of the imaging device deactivated based on the physiological condition of the anatomical region.

2. The system of claim 1, wherein the imaging device is one of an ultrasound transducer, a scope, or an X-ray gantry.

3. The system of claim 1, further comprising:
   a robot configured to position the imaging device,
   wherein the controller is further configured to control the robot to position the imaging device.

4. The system of claim 1, wherein the controller is further configured to decrease a frequency of activating the imaging functionality of the imaging device in response to physiological parameter data indicating a delineated improvement in the physiological condition of the anatomical region.

5. The system of claim 1, wherein the controller is further configured to increase a frequency of activating the imaging functionality of the imaging device in response to physiological parameter data indicating a delineated deterioration in the physiological condition of the anatomical region.

6. The system of claim 1, wherein the controller is further configured to decrease a duty cycle of activating the imaging functionality of the imaging device in response to physiological parameter data indicating a delineated improvement in the physiological condition of the anatomical region.

7. The system of claim 1, wherein the controller is further configured to increase a duty cycle of activating the imaging functionality of the imaging device in response to physiological parameter data indicating a delineated deterioration in the physiological condition of the anatomical region.

8. The system of claim 1, wherein the controller is further configured to control a degree of contact force applied by the imaging device to an anatomical structure within the anatomical region.

9. The system of claim 8, wherein the controller is further configured to control the degree of contact force applied by the imaging device to the anatomical structure based on activation of the imaging functionality of the imaging device.

10. A controller for positioning an imaging device relative to an anatomical region, the controller comprising:
    a processor communicatively coupled to memory, the processor configured to:
       in response to generation of an image of the anatomical region by the imaging device, extract a physiological condition of the anatomical region from the image of the anatomical region, and
       adapt cycling of the positioning of the imaging device between a position with imaging functionality of the imaging device activated and a position with the imaging functionality of the imaging device deactivated based on the physiological condition of the anatomical region.

11. The controller of claim 10, wherein the processor is further configured to control a robot to position the imaging device.

12. The controller of claim 10, wherein the processor is further configured to control a degree of contact force applied by the imaging device to an anatomical structure within the anatomical region.

13. The controller of claim 12, wherein the processor is further configured to control the degree of contact force applied by the imaging device to the anatomical structure based on activation of the imaging functionality of the imaging device.

14. The controller of claim 10, wherein the processor is further configured to increase a frequency of activating the imaging functionality of the imaging device in response to physiological parameter data indicating a delineated deterioration in the physiological condition of the anatomical region.

15. The controller of claim 10, wherein the processor is further configured to decrease a duty cycle of activating the imaging functionality of the imaging device in response to physiological parameter data indicating a delineated improvement in the physiological condition of the anatomical region.

16. The controller of claim 10, wherein the processor is further configured to increase a duty cycle of activating the imaging functionality of the imaging device in response to physiological parameter data indicating a delineated deterioration in the physiological condition of the anatomical region.

17. A method for positioning an imaging device relative to an anatomical region, the method comprising:
    in response to generation of an image of the anatomical region by the imaging device, extract a physiological condition of the anatomical region from the image of the anatomical region; and
    adapting cycling of the positioning of the imaging device between a position with imaging functionality of the imaging device activated and a position with the imaging functionality of the imaging device deactivated based on the physiological condition of the anatomical region.

18. The method of claim 17, further comprising:
    controlling a robot to position the imaging device.

19. The method of claim 17, further comprising:
    controlling a degree of contact force applied by the imaging device to an anatomical structure within the anatomical region.

20. The method of claim 19, further comprising:
    controlling the degree of contact force applied by the imaging device to the anatomical structure based on activation of the imaging functionality of the imaging device.

* * * * *